US008980938B2

(12) United States Patent
Hachtel et al.

(10) Patent No.: US 8,980,938 B2
(45) Date of Patent: *Mar. 17, 2015

(54) CXCR2 INHIBITORS

(75) Inventors: Stephanie Hachtel, Frankfurt (DE); Juergen Dedio, Frankfurt (DE); Josef Pernerstorfer, Frankfurt (DE); Stephen Shimshock, Hillsborough, NJ (US); Carolina Lanter, Audubon, PA (US)

(73) Assignee: Sanofi, Paris (FR)

( * ) Notice: Subject to any disclaimer, the term of this patent is extended or adjusted under 35 U.S.C. 154(b) by 1306 days.

This patent is subject to a terminal disclaimer.

(21) Appl. No.: 12/337,980

(22) Filed: Dec. 18, 2008

(65) Prior Publication Data

US 2009/0258936 A1    Oct. 15, 2009

Related U.S. Application Data

(63) Continuation of application No. PCT/EP2007/005577, filed on Jun. 25, 2007.

(30) Foreign Application Priority Data

Jun. 30, 2006  (EP) .................................... 06013591

(51) Int. Cl.
| A01N 43/12 | (2006.01) |
| A61K 31/38 | (2006.01) |
| A01N 43/02 | (2006.01) |
| C07D 333/52 | (2006.01) |
| C07D 333/72 | (2006.01) |
| C07D 409/02 | (2006.01) |
| C07D 333/16 | (2006.01) |
| C07C 235/66 | (2006.01) |
| C07D 333/54 | (2006.01) |

(52) U.S. Cl.
CPC ............ C07D 333/16 (2013.01); C07C 235/66 (2013.01); C07D 333/54 (2013.01); C07C 2101/14 (2013.01); C07C 2102/10 (2013.01)
USPC .............................. 514/443; 514/430; 549/51

(58) Field of Classification Search
USPC ..................... 514/443, 430; 549/51
See application file for complete search history.

(56) References Cited

U.S. PATENT DOCUMENTS

| 4,962,224 A | 10/1990 | Wrobel et al. |
| 4,994,477 A | 2/1991 | Kempf et al. |
| 7,919,628 B2 | 4/2011 | Hachtel et al. |
| 2002/0123522 A1 | 9/2002 | Fritz et al. |
| 2004/0204417 A1 | 10/2004 | Perez et al. |
| 2005/0059705 A1 | 3/2005 | Mjalli et al. |
| 2008/0090854 A1 | 4/2008 | Hachtel et al. |

FOREIGN PATENT DOCUMENTS

| EP | 1676834 | 7/2006 |
| FR | 2825706 | 12/2002 |
| WO | WO 99/07351 | 2/1999 |
| WO | WO01/58852 | 8/2001 |
| WO | WO2004/108681 | 12/2004 |
| WO | WO2005/023818 | 3/2005 |
| WO | WO2005/033102 | 4/2005 |
| WO | WO2005/051940 | 6/2005 |
| WO | WO2005/070906 | 8/2005 |
| WO | WO2006/040646 | 4/2006 |
| WO | WO2006/052722 | 5/2006 |
| WO | WO2006/099610 | 9/2006 |

OTHER PUBLICATIONS

Boschelli D.H. et al., "Inhibition of E-Selectin-, ICAM-1-, and VCAM-1-Mediated Cell Adhesion by Benzo[b]thiophene-, Benzofuran-, Indole-, and Naphthalene-2-Carboxamides: Identification of PD 144795 as an Antiinflammatory Agent", Journal of Medicinal Chemistry, 38:4597-4614 (1995).
International Search Report dated Mar. 29, 2006 corresponding to International Application No. PCT/EP2005/013624 from related U.S. Appl. No. 13/079,522.
U.S. Office Action dated Nov. 18, 2011 received in related U.S. Appl. No. 13/079,522.
Kubinyi H., "3D QSAR in Drug Design: Ligand-Protein Interactions and Molecular Similarity", vol. 2-3, Springer, 1998, 800 pages, pp. 243-244 provided.
Wermuth, The Practice of Medicinal Chemistry, 2d ed., 768 pages, Chapters 9-10 provided, 2003.
International Search Report dated Oct. 2, 2007 corresponding to International Application No. PCT/EP2007/005576 from related U.S. Appl. No. 12/337,040.

(Continued)

Primary Examiner — Samira Jean-Louis
(74) Attorney, Agent, or Firm — Scully, Scott, Murphy & Presser, P.C.

(57) ABSTRACT

The invention relates to compounds of the formula I

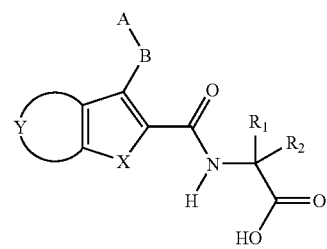

in which R1, R2, A, B, X and Y have the meanings indicated in the claims, and/or a pharmaceutically acceptable salt and/or a prodrug thereof. Because of their properties as inhibitors of chemokine receptors, especially as CXCR2 inhibitors, the compounds of the formula I and the pharmaceutically acceptable salts and prodrugs thereof are suitable for the prevention and treatment of chemokine mediated diseases.

15 Claims, No Drawings

(56) References Cited

OTHER PUBLICATIONS

U.S. Office Action dated Jan. 12, 2012 received in related U.S. Appl. No. 12/337,040.

Jodlbauer J. et al., "Towards Ochratoxin a Selective Molecularly Imprinted Polymers for Solid-Phase Extraction", *Journal of Chromatography A*, 945(1-2):45-63 (2002).

U.S. Office Action dated Sep. 26, 2011 received in related U.S. Appl. No. 12/337,040.

Van den Eynde et al., Database Caplus Chemical Abstracts Service, Columbus, Ohio, US; Database Accession No. 1972:47393, Abstract, DE 2108189, Sep. 9, 1971.

International Search Report dated Sep. 14, 2007 corresponding to International Application No. PCT/EP2007/005574 from related U.S. Appl. No. 12/337,107.

U.S. Final Office Action dated Feb. 29, 2012 received in related U.S. Appl. No. 12/337,107.

Huff J.R., "HIV Protease: A Novel Chemotherapeutic Target for AIDS", *Journal of Medicinal Chemistry*, 34(8):2305-2314 (Aug. 1991).

The Merck Manual of Diagnosis and Therapy (16$^{th}$ Ed., pp. 52-55) (1999).

Johnson J. et al., "Relationships Between Drug Activity in NCI Preclinical In Vitro and In Vivo Models and Early Clinical Trials", *British Journal of Cancer*, 84(10):1424-1431 (2001).

Lala P.K. et al., "Role of Nitric Oxide in Tumor Progression: Lessons from Experimental Tumors", *Cancer and Metastasis Reviews*, 17:91-106 (1998).

Sausville E.A. et al., "Contributions of Human Tumor Xenografts to Anticancer Drug Development", *Cancer Research* 66(7):3351-3354 (Apr. 1, 2006).

Golub T.R. et al., "Molecular Classification of Cancer: Class Discovery and Class Prediction by Gene Expression Monitoring", *Science*, 286:531-537 (1999).

U.S. Office Action dated Jul. 12, 2011 received in related U.S. Appl. No. 12/337,107.

International Search Report dated Sep. 3, 2007 corresponding to International Application No. PCT/EP2007/005575 from related U.S. Appl. No. 12/337,970.

U.S. Final Office Action dated Feb. 8, 2012 received in related U.S. Appl. No. 12/337,970.

U.S. Office Action dated Sep. 15, 2011 received in related U.S. Appl. No. 12/337,970.

CXCR2 INHIBITORS

Chemokines are a family of low molecular weight proteins (8-13 kDa) that are classified into four distinct groups depending on the positioning of the cysteine motif at the amino terminus. The family members comprise CXC, CC, XC, and CX3C chemokines of which CXC and CC are the largest and most characterized. The CXC chemokines include interleukin-8 (IL-8), neutrophil-activating protein-2 (NAP-2), growth-related oncogenes GRO-α, GRO-β, GRO-γ, epithelial cell-derived neutrophil activating factor-78 (ENA-78), granulocyte chemoattractant protein-2 (GCP-2), γ-interferon-inducible protein-10 (γIP-10), interferon-inducible T cell α-chemoattractant (I-TAC), monokine induced by γ-interferon (Mig) and platelet factor-4 (PF-4). CC chemokines include RANTES (regulated on activation normal T cell expressed and secreted), macrophage inflammatory proteins MIP-1α, MIP-1γ, monocyte chemoattractant proteins MCP-1, MCP-2, MCP-3 and eotaxin. The XC family comprises two members, lymphotactin-α and lymphotactin-β, and the CX3C family consists only of a single chemokine named fractalkine (Murphy et al., Pharmacol. Rev. 52: 145-176, 2000).

Chemokines mediate their biological effects by binding to cell surface molecules, which belong to the superfamily of seven-transmembrane spanning receptors that signal through coupling to heterotrimeric G proteins. Although most chemokine receptors recognize more than one chemokine, they are almost always restricted to a single subclass. Chemokine receptor binding initiates a cascade of intracellular events of which the first step is the binding of the receptor by its high-affinity ligand. This induces a conformational change leading to a dissociation of the receptor-associated heterotrimeric G proteins into α and βγ subunits. These G protein subunits are able to activate various effector proteins, including phospholipases leading to generation of inositol trisphosphate, an increase in cytosolic calcium, and activation of protein kinases. This cascade of intracellular events mediates a wide range of functions in different leukocytes such as chemotaxis, degranulation, oxidative burst, phagocytosis, and lipid mediator synthesis.

Interleukin-8 (IL-8) is a key mediator of immunological reactions in inflammatory disorders such as atherosclerosis, ischemia/reperfusion injury, rheumatoid arthritis, chronic obstructive pulmonary disease, respiratory distress syndrome, asthma, cystic fibrosis, and psoriasis (Bizarri et al., Curr. Med. Chem. 2: 67-79, 2003). IL-8 is the most characterized member of the CXC subfamily of chemokines. Leukocyte responses to IL-8 are mediated via specific cell surface receptors, CXCR1 and CXCR2. Whereas CXCR1 is selectively activated by IL-8, CXCR2 responds to several additional chemokines including growth-related oncogenes GRO-α, GRO-β, GRO-γ, neutrophil-activating protein-2 (NAP-2), epithelial cell-derived neutrophil activating factor-78 (ENA-78), and granulocyte chemoattractant protein-2 (GCP-2). The common denominator shared by all chemokines that activate CXCR2 is a Glu-Leu-Arg (ELR) sequence in the amino terminus, which appears to serve as a recognition sequence for receptor binding and activation (Herbert et al., J. Biol. Chem. 266: 18989-18994, 1991).

Early investigations concentrated on the effect of IL-8 on neutrophils, which respond to IL-8 with calcium mobilization, actin polymerization, enzyme release, chemotaxis, and the respiratory burst. Despite similar affinities for IL-8 and similar receptor numbers of CXCR1 and CXCR2 on neutrophils, both receptors are functionally different. Responses such as calcium mobilization and the release of granule enzymes are mediated through both receptors, whereas the respiratory burst and the activation of phospholipase D depend exclusively on stimulation of CXCR1 (Jones et al., Proc. Natl. Acad. Sci. USA 93: 6682-6686, 1996). Due to their prominent role in neutrophil recruitment, CXCR1 and CXCR2 are thought to be important in several acute neutrophil-mediated diseases such as acute respiratory distress syndrome and ischemia/reperfusion injuries, as well as in chronic diseases such as asthma, psoriasis, dermatitis, and arthritis.

It has been shown that CXCR2 is also expressed by monocytes. Despite IL-8's inactivity in monocyte chemotaxis assay, this factor induces calcium flux and respiratory burst in monocytes and enhances adhesion of monocytes in static assays. Similarly, GRO-α enhances adhesion of monocytes to stimulated endothelial cells. Moreover, IL-8 is able to induce firm arrest of monocytes on endothelial cells under conditions of physiological flow (Gerszten et al., Nature 398: 718-723, 1999). Since CXCR2 is strongly expressed on monocytes and macrophages in atherosclerotic lesions where it is suggested to play a key role in chemoattraction, retension, expansion, and activation of monocytes and macrophages, this strongly suggests that CXCR2 and one or more of its ligands (IL-8, GRO-α) play a pathophysiological role in atherosclerosis (Huo et al., J. Clin. Invest. 108: 1307-1314, 2001).

Apart from neutrophils and monocytes, numerous cell types have been shown to express IL-8 receptors. These cell types include neurons, various cancer cells, keratinocytes, and endothelial cells. Several lines of evidence indicate that IL-8 plays a direct role in angiogenesis via stimulation of CXCR2 expressed on endothelial cells. IL-8 has been shown to bind specifically to endothelial cells and induce chemotaxis. IL-8 is able to induce neovascularization in the absence of inflammatory responses (Koche et al., Science 258: 1798-1801, 1992). Moreover, there is accumulating evidence that IL-8 could play a key role in melanoma progression and metastasis as patients with melanoma metastases have elevated serum levels of IL-8. IL-8 is supposed to act as an autocrine growth and metastatic factor for melanoma cells (Schadendorf et al., J. Immunol: 151-157, 1993).

Due to the wide range of actions of IL-8, such as attraction and activation of neutrophils and monocytes/macrophages as well as promotion of endothelial cell proliferation and cancer cell growth, the inhibition of chemokine receptors CXCR1 and CXCR2 is expected to be beneficial in the prevention and treatment of numerous diseases. Besides acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases include adult respiratory distress syndrome, inflammatory bowel disease, ulcerative colitis, Crohn's disease, atopic dermatitis, cystic fibrosis, psoriasis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

WO 2006/040646 (Pfizer) describes Benzimidazole or Indole amides useful in the treatment of abnormal cell growth, in particular cancer. WO 2006/052722 (Smithkline Beecham) relates to mono or bicyclic amide derivatives of formula (I) useful as inhibitors of glycogen phosphorylase having a different connecting group and substitution pattern at the condensed ring system. EP 1676834 (Sanofi-Aventis) describes fused aromatic compounds which are different from the present non-aromatic carboxamides derivatives.

WO 01/58852 (Dompe) describes N-(2-aryl-propionyl) amides of formula (I) useful in the inhibition of neutrophils induced by II-8.

The invention provides novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

The invention relates to a compound of formula I

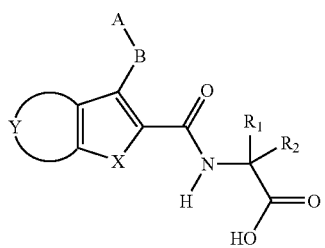

wherein
X is —CR3=CR4-, —CR5=N—, —N=CR6-, —NR7- or —S—;
R3, R4, R5 and R6
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, NO₂, NR27R28, C(O)R29, C(O)NR30R31, S(O)₀R32, S(O)ₚNR33R34, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34
are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p
are, independently of one another, 1 or 2;
R7 is hydrogen, alkyl having 1, 2, 3 or 4 carbon atoms or C(O)R35;
R35 is hydrogen, alkyl with 1, 2, 3 or 4 carbon atoms or aryl;
Y is —C(R61R62)-C(R61R62)-C(R61R62)-, —S(O)ᵤ—C(R63R64)-C(R61R62)-, —C(R63R64)-S(O)ᵤ—C(R63R64)-, —C(R61R62)-C(R63R64)-S(O)ᵤ—C(R61R62)-C(R61R62)-C(R61R62)-, —S(O)ᵤ—C(R63R64)-C(R61R62)-C(R61R62)-,
—C(R63R64)-S(O)ᵤ—C(R63R64)-C(R61R62)-,
—C(R61R62)-C(R63R64)-S(O)ᵤ—C(R63R64)-,
—C(R61R62)-C(R61R62)-C(R63R64)-S(O)ᵤ—,
—S(O)ᵤ—C(R63R64)-C(R63R64)-S(O)ᵤ—, —S(O)ᵥ—CR65=CR66- or —CR67=CR68-S(O)ᵥ—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or SCF₃;
R62, R63 and R64
are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, NO₂, CN or SCF₃;
u is 0, 1 or 2;
v is 0, 1 or 2;
A is cycloalkyl having 3, 4, 5, 6, 7 or 8 carbon atoms, heterocyclyl having 5, 6, 7 or
8 atoms, phenyl or heteroaryl having 5 or 6 atoms;
in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms,
and in which said cycloalkyl, heterocyclyl, phenyl or heteroaryl and
the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms or —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is a linear linker consisting of 3, 4 or 5 carbon atoms, in which 1 or 2 carbon atoms can be replaced by a member of a heteroatom containing group consisting of O, NR19 or $S(O)_y$, and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which
1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46
are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is hydrogen or alkyl having 1, 2, 3, 4, 5 or 6 carbon atoms;
which can be unsubstituted or substituted by 1, 2, 3, 4 or 5 radicals
selected from the group consisting of F, Cl, Br, I, $—O_i—(CH_2)_j—R25$;
i is 0 or 1;
j is 0, 1, 2 or 3;
R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4 5, 6, 7 or 8 atoms;
wherein alkyl is unsubstituted or substituted by 1, 2, 3, 4 or 5 radicals selected from the group consisting of F, Cl, Br, I, $—O_m—(CH_2)_n—R26$;
m is 0, or 1;
n is 0, 1, 2 or 3;
R26 is hydrogen, phenyl, heteroaryl having 5 or 6 atoms, cycloalkyl having 3, 4, 5 or 6 carbon atoms or heterocyclyl
having 3, 4 5, 6, 7 or 8 atoms, in which the phenyl, heteroaryl, cycloalkyl or heterocyclyl are unsubstituted or substituted by 1, 2, or 3 radicals selected from F, Cl, Br or I;
and wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

or

R1 and R2
form, together with the carbon atom to which they are attached, a 3-, 4-, 5- or 6-membered carbon ring, wherein one carbon atom, which is not adjacent to the carbon atom, to which R1 and R2 are attached, can be replaced by —O—, —NR58- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;
wherein the formed ring and the condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$, SCF$_3$, SF$_5$, or alkyl having 1, 2, 3 or 4 carbon atoms;
R58 is hydrogen, alkyl having 1, 2, 3 or 4 carbon atoms or C(O)R59;
R59 is hydrogen, alkyl with 1, 2, 3 or 4 carbon atoms or phenyl;
w is 0, 1 or 2;

and/or a pharmaceutically acceptable salt and/or a prodrug thereof.

Preference is given to a compound of the formula I, in which:

X is —CR3=CR4-, —CR5=N—, —N=CR6-, —NR7- or —S—;
R3, R4, R5 and R6 are, independently of one another, hydrogen, F, Cl, Br, I, alkyl having 1, 2, 3 or 4 carbon atoms or alkoxy having 1, 2, 3 or 4 carbon atoms;
R7 is hydrogen or alkyl having 1, 2, 3 or 4 carbon atoms;
Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or SCF$_3$;
R62, R63 and R64
are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, NO$_2$, CN or SCF$_3$;
A is cycloalkyl having 3, 4, 5, 6, 7 or 8 carbon atoms, heterocyclyl having 5, 6, 7 or 8 atoms, phenyl or heteroaryl having 5 or 6 atoms;
in which the said phenyl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms,
and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, NO$_2$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10, or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—; —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)-C(R15R16)- or —O—C(R13R14)-C(R13R14)-O—C(R13R14)-;

with the proviso that, if A is connected to the linker B via a nitrogen atom being part of A, the atom of the linker which is connected to A is a carbon atom;

R11 and R12 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2;

R1 is hydrogen or alkyl having 1, 2, 3, 4, 5 or 6 carbon atoms; and

R2 is alkyl having 1, 2, 3, 4, 5 or 6 carbon atoms or phenyl, wherein alkyl is unsubstituted or substituted by 1, 2, 3, 4 or 5 radicals selected from the group consisting of F, Cl, Br, I, —O$_m$—(CH$_2$)$_n$—R26;

m is 0, or 1;

n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4, 5, 6, 7 or 8 atoms; in which the phenyl, heteroaryl, cycloalkyl or heterocyclyl are unsubstituted or substituted by 1, 2, or 3 radicals selected from F, Cl, Br or I;

or

R1 and R2 form, together with the carbon atom to which they are attached, a 3-, 4-, 5- or 6-membered saturated or partly saturated carbon ring, which can be condensed to phenyl;

or

R1 and R2
    form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NH— or —S—;

and/or a pharmaceutically acceptable salt and/or prodrug thereof.

Particular preference is given to a compound of the formula I in which:

X is —CR3=CR4-, —CR15=N—, —N=CR6-, —NH— or —S—;
    R3, R4, R5 and R6
        are, independently of one another, hydrogen, F, Cl or Br;
Y is —C(R61R62)-C(R61R62)-C(R61R62)-, —S—C(R63R64)-C(R61R62)-, —C(R63R64)-S—C(R63R64)-, —C(R61R62)-C(R63R64)-S——C(R61R62)-C(R61R62)-C(R61R62)-C(R61R62)-, —S—C(R63R64)-C(R61R62)-C(R61R62)-, —C(R63R64)-S—C(R63R64)-C(R61R62)-, —C(R61R62)-C(R63R64)-S—C(R63R64)-, —C(R61R62)-C(R61R62)-C(R63R64)-S—, —S—C(R63R64)-C(R63R64)-S—, —S—CR65=CR66- or —CR67=CR68-S—;
    R61, R62, R63 and R64
        are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
    with the proviso, that in any embodiment of Y a maximum of 4 of the substituents R61 to R64 are not hydrogen;
    R65, R66, R67 and R68
        are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
A is cycloalkyl having 3, 4, 5, 6, 7 or 8 carbon atoms, heterocyclyl having 5, 6, 7 or 8 atoms, phenyl or heteroaryl having 5 or 6 atoms;
    in which the said phenyl can be condensed to form a naphthyl or an indanyl;
        in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, $NO_2$, $SF_5$, $SCF_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—,
    with the proviso, that if A is connected to the linker via a nitrogen atom being part of A, the atom of the linker which is connected to A is a carbon atom;
    R11-R18 are, independently of one another, hydrogen, F or alkyl having 1, 2, 3, 4 carbon atoms
    R19 is H or alkyl having 1, 2, 3, 4, 5 or 6 carbon atoms.
R1 is alkyl having 1, 2, 3 or 4 carbon atoms;
and
R2 is alkyl having 1, 2, 3 or 4 carbon atoms, phenyl or benzyl;
or
R1 and R2
    form, together with the carbon atom to which they are attached, a cyclopropane, cyclobutane, cyclopentane, cyclohexane, cyclopentene ring or indene;
or
R1 and R2
    form, together with the carbon atom to which they are attached, a tetrahydro-thiophene or tetrahydro-thiopyrane ring;
and/or a pharmaceutically acceptable salt and/or prodrug thereof.

Special preference is given to a compound of the formula I, in which
X is —CR3=CR4- or —S—;
    R3 and R4
        are, independently of one another, hydrogen, F, Cl or Br;
Y is —C(R61R62)-C(R61R62)-C(R61R62)-, —C(R61R62)-C(R61R62)-C(R61R62)-C(R61R62)-, —S—CR65=CR66- or —CR67=CR68-S—;
    R61 and R62
        are, independently of one another, hydrogen, F or alkyl having 1, 2, 3 or 4 carbon atoms;
    with the proviso, that in any embodiment of Y a maximum of 4 of the substituents R61 to R62 are not hydrogen;
    R65, R66, R67 and R68
        are, independently of one another, hydrogen, F, Cl, Br, I, alkyl having 1, 2, 3 or 4 carbon atoms;
A is cyclohexyl, phenyl, naphthyl, indanyl or thienyl;
    in which the phenyl radical is unsubstituted or substituted by 1, 2 or 3 radicals selected from the group consisting of F, Cl, Br, methoxy, methyl, ethyl, propyl, iso-propyl or trifluoromethyl;
B is —C(R11R12)-C(R13R14)-O—, —C(R11R12)-C(R15R16)-C(R13R14)-O—, —O—C(R13R14)-C(R13R14)-O—, —C(R11R12)-C(R15R16)-C(R15R16)-C(R13R14)-O—, —O—C(R13R14)-C(R15R16)-C(R13R14)-O—, or —C(R13R14)-O—C(R13R14)-C(R13R14)-O—,
    R11-R16 are, independently of each other, hydrogen or methyl;
R1 is methyl or ethyl;
and
R2 is methyl or ethyl;
or
R1 and R2
    form, together with the carbon atom to which they are attached, a cyclobutane or cyclopentane ring;
and/or a pharmaceutically acceptable salt and/or a prodrug thereof.

More special preference is given to a compound of the formula I, in which
X is —CR3=CR4-;
    R3 and R4
        are, independently of one another, hydrogen or F;

Y is —C(R61R62)-C(R61R62)-C(R61R62)-C(R61R62)-, —S—CR65=CR66- or —CR67=CR68-S—;
R61 and R62
are, independently of one another, hydrogen or F;
with the proviso, that in any embodiment of Y a maximum of 4 of the substituents R61 to R62 are not hydrogen;
R65, R66, R67 and R68
are, independently of one another, hydrogen, F, Cl, Br, I, alkyl having 1, 2, 3 or 4 carbon atoms;
A is cyclohexyl, phenyl or thienyl;
in which the phenyl radical is unsubstituted or substituted by 1, 2 or 3 radicals selected from the group consisting of F, Cl, Br, methoxy, methyl, ethyl, propyl, iso-propyl or trifluoromethyl;
B is —C(R11R12)-C(R13R14)-O—, —C(R11R12)-C(R15R16)-C(R13R14)-O——O—C(R13R14)-C(R13R14)-O—, —C(R11R12)-C(R15R16)-C(R15R16)-C(R13R14)-O or —O—C(R13R14)-C(R15R16)-C(R13R14)-O—;
R11-R16 are, independently of each other, hydrogen or methyl;
R1 is methyl;
and
R2 is methyl or ethyl;
and/or a pharmaceutically acceptable salt and/or a prodrug thereof.

Even more special preference is given to a compound of the formula I, in which
X is —CR3=CR4-;
R3 and R4
are, independently of one another, hydrogen or F;
Y is —C(R61R62)-C(R61R62)-C(R61R62)-C(R61R62)-,
R61 and R62 are, independently of one another, hydrogen or F; with the proviso, that in any embodiment of Y a maximum of 4 of the substituents R61 to R62 are not hydrogen;
A is cyclohexyl, phenyl or thienyl;
in which the phenyl radical is unsubstituted or substituted by 1, 2 or 3 radicals selected from the group consisting of F, Cl, Br, methoxy, methyl, ethyl, propyl, iso-propyl or trifluoromethyl;
B is —C(R11R12)-C(R13R14)-O—, —O—C(R13R14)-C(R13R14)-O—, —C(R11R12)-C(R15R16)-C(R15R16)-C(R13R14)-O or —O—C(R13R14)-C(R15R16)-C(R13R14)-O—;
R11-R16 are, independently of each other, hydrogen or methyl;
R1 is methyl;
and
R2 is methyl or ethyl;
and/or a pharmaceutically acceptable salt and/or a prodrug thereof.

In one embodiment X in compounds of formula I is described by —CR3=CR4-, —CR5=N—, —N=CR6-, —NR7- or —S—, wherein R3, R4, R5 and R6 are independently of one another, hydrogen, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen; preference is given to compounds, in which X is described by —CR3=CR4-, —CR5=N—, —N=CR6-, —NH— or —S—, wherein R3, R4, R5 and R6 are, independently of one another, hydrogen, F, Cl, Br I or alkyl having 1, 2, 3 or 4 carbon atoms, preferably R3, R4, R5 and R6 are, independently of one another, hydrogen, F, Cl or Br; particular preference is given to compounds, in which X is described as —CR3=CH—, —CH=N—, —N=CH, NH or —S—, wherein R3 is defined as hydrogen, F, Cl or Br; more particular preference is given to compounds, in which X is described as —CR3=CH— or —S—, wherein R3 is defined as hydrogen, F, Cl or Br.; most particular preference is given to compounds, in which X is described as —CR3=CH—, wherein R3 is defined as hydrogen or F.

X is attached with its left hand side to the carbon atom being directly connected to the Y— ring and with its right hand side to the other carbon atom.

In a further embodiment of compounds of formula I
Y is —C(R61R62)-C(R61R62)-C(R61R62)-, —S—C(R63R64)-C(R61R62)-, —C(R63R64)-S—C(R63R64)-, —C(R61R62)-C(R63R64)-S——C(R61R62)-C(R61R62)-C(R61R62)-C(R61R62)-, —S—C(R63R64)-C(R61R62)-C(R61R62)-, —C(R63R64)-S—C(R63R64)-C(R61R62)-, —C(R61R62)-C(R63R64)-S—C(R63R64)-, —C(R61R62)-C(R61R62)-C(R63R64)-S—, —S—C(R63R64)-C(R63R64)-S—, —S—CR65=CR66- or —CR67=CR68-S—;
R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;
R62, R63 and R64
are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$.

In a preferred embodiment of compounds of formula I

Y is —C(R61R62)-C(R61R62)-C(R61R62)-, —S—C(R63R64)-C(R61R62)-, —C(R63R64)-S—C(R63R64)-, —C(R61R62)-C(R63R64)-S—C(R61R62)-C(R61R62)-C(R61R62)-, —S—C(R63R64)-C(R61R62)-C(R61R62)-, —C(R63R64)-S—C(R63R64)-C(R61R62)-, —C(R61R62)-C(R63R64)-S—C(R63R64)-, —C(R61R62)-C(R61R62)-C(R63R64)-S—, —S—C(R63R64)-C(R63R64)-S—, —S—CR65=CR66- or —CR67=CR68-S—;

R61, R62, R63 and R64
are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
with the proviso, that in any embodiment of Y a maximum of 4 of the substituents R61 to R64 are not hydrogen;

R65, R66, R67 and R68
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

In a more preferred embodiment of compounds of formula I
Y is —C(R61R62)-C(R61R62)-C(R61R62)-, —C(R61R62)-C(R61R62)-C(R61R62)-C(R61R62)-, —S—CR65=CR66- or —CR67=CR68-S—;

R61 and R62
are, independently of one another, hydrogen, F or alkyl having 1, 2, 3 or 4 carbon atoms;
with the proviso, that in any embodiment of Y a maximum of 4 of the substituents R61 to R62 are not hydrogen;
preferably, R61 and R62
are, independently of one another, hydrogen or F;
with the proviso, that in any embodiment of Y a maximum of 4 of the substituents R61 to R62 are not hydrogen;
more preferably, R61 and R62 are hydrogen;

R65, R66, R67 and R68
are, independently of one another, hydrogen, F, Cl, Br or alkyl having 1, 2, 3 or 4 carbon atoms;
preferably R65, R66, R67 and R68
are, independently of one another, hydrogen or F; more preferably, hydrogen.

In a most preferred embodiment of compounds of formula I
Y is —C(R61R62)-C(R61R62)-C(R61R62)-C(R61R62)-,
R61 and R62
are, independently of one another, hydrogen, F or alkyl having 1, 2, 3 or 4 carbon atoms;
with the proviso, that in any embodiment of Y a maximum of 4 of the substituents R61 to R62 are not hydrogen;
preferably R61 and R62
are, independently of one another, hydrogen or F;
with the proviso, that in any embodiment of Y a maximum of 4 of the substituents R61 to R62 are not hydrogen;
more preferably, Y is —CH$_2$—CH$_2$—CH$_2$—CH$_2$—.

Y is attached with its right hand side to the carbon atom connected to X and with its left hand side to the other carbon atom.

In a further embodiment of the compounds of formula I
A is cycloalkyl having 3, 4, 5, 6, 7 or 8 carbon atoms, heterocyclyl having 5, 6, 7 or 8 atoms, phenyl or heteroaryl having 5 or 6 atoms;

in which the said phenyl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms;
preferably, the said phenyl is not condensed or condensed to form a naphthyl or an indanyl, more preferably, the said phenyl is not condensed;
and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, NO$_2$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms.

In a preferred embodiment of compounds of formula I
A is cycloalkyl having 3, 4, 5, 6, 7 or 8 carbon atoms, heterocyclyl having 5, 6, 7 or 8 atoms, phenyl or heteroaryl having 5 or 6 atoms;
in which the said phenyl can be condensed to form a naphthyl or an indanyl,
more preferably, the said phenyl is not condensed;
in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, NO$_2$, SF$_5$, SCF$_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
preferably they are unsubstituted or substituted by 1, 2 or 3 radicals selected from the group consisting of F, Cl, Br, methoxy, alkyl having 1, 2 or 3 carbon atoms in which 1, 2, 3, 4, 5, 6 or 7 hydrogen atoms may be substituted by fluorine atoms.

In a more preferred embodiment,
A is cyclohexyl, piperidyl, phenyl, naphthyl, indanyl, thienyl, pyridinyl or imidazolyl;
in which the phenyl radical is unsubstituted or substituted by 1, 2 or 3 radicals selected from the group consisting of F, Cl, Br, methoxy, alkyl having 1, 2 or 3 carbon atoms in which 1, 2, 3, 4, 5, 6 or 7 hydrogen atoms may be substituted by fluorine atoms;
in which pyridinyl is unsubstituted or substituted by Cl;
preferably, phenyl is unsubstituted or substituted by 1 radical selected from F, Cl, methyl or trifluoromethyl; more preferably, phenyl is unsubstituted or substituted by fluorine.

In an even more preferred embodiment
A is cyclohexyl, phenyl, naphthyl, indanyl or thienyl;
in which the phenyl radical is unsubstituted or substituted by 1, 2 or 3 radicals selected from the group consisting of F, Cl, Br, methoxy, methyl, ethyl, propyl, iso-propyl or trifluoromethyl;
preferably, phenyl is unsubstituted or substituted by 1 radical selected from F, Cl, methyl or trifluoromethyl; more preferably, phenyl is unsubstituted or substituted by fluorine.

In a most preferred embodiment
A is cyclohexyl, phenyl or thienyl,
in which the phenyl radical is unsubstituted or substituted by 1, 2 or 3 radicals selected from the group consisting of F, Cl, Br, methoxy, methyl, ethyl, propyl, iso-propyl or trifluoromethyl;
preferably, phenyl is unsubstituted or substituted by 1 radical selected from F, Cl, methyl or trifluoromethyl; more preferably, phenyl is unsubstituted or substituted by fluorine.

In some of the embodiments of A there is the possibility that A is cycloalkyl having 3, 4, 5, 6, 7 or 8 carbon atoms, heterocyclyl having 5, 6, 7 or 8 atoms, phenyl or heteroaryl having 5 or 6 atoms in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms. Representative examples for condensed radicals resulting from the mentioned combinations are given in the list below. In case where two different radicals are condensed the examples apply to both situations, where either the one or the other ring in the condensed radical is attached to B. For example, if cycloalkyl is attached to B and is condensed with a heterocyclyl, the same examples also apply to the situation where heterocyclyl is attached to B and is condensed with a cycloalkyl;

Cycloalkyl-cycloalkyl:
Octahydro-pentalene, bicyclo[4.1.0]heptane, octahydro-indene, decahydro-naphthalene, decahydro-azulene Cycloalkyl-heterocyclyl:
Hexahydro-cyclopenta[b]furane, 7-oxa-bicyclo[4.1.0]heptane, octahydro-cyclopenta[1,4]oxazine, octahydro-benzo[1,4]dioxine, octahydro-cyclohepta[b]thiophene;

Cycloalkyl-phenyl:
Bicyclo[4.2.0]octa-1,3,5-triene, indane, 1,2,3,4-tetrahydro-naphthalene, 6,7,8,9-tetrahydro-5H-benzocycloheptene, 5,6,7,8,9,10-hexahydro-benzocyclooctene;

Cycloalkyl-heteroaryl:
6,7-Dihydro-5H-[1]pyrindine, 5,6,7,8-tetrahydro-isoquinoline, 6,7,8,9-tetrahydro-5H-cyclohepta[b]pyridine, 4,5,6,7-tetrahydro-benzooxazole, 4,5,6,7-tetrahydro-benzo[b]thiophene;

Heterocyclyl-heterocyclyl:
Hexahydro-pyrrolizine, 3,7-dioxa-bicyclo[4.1.0]heptane, octahydro-pyrano[3,2-b]pyridine, hexahydro-furo[3,2-b]pyrane, hexahydro-1,4-dioxa-6-thia-naphthalene;

Heterocyclyl-phenyl:
2,3-Dihydro-benzofuran, benzo[1,3]dioxole, 1,2,3,4-tetrahydro-isoquinoline, 2,3,4,5-tetrahydro-1H-benzo[b]azepine, 2,3-dihydro-benzo[d]isoxazole;

Heterocyclyl-heteroaryl:
5,6,7,8-Tetrahydro-4H-thieno[3,2-c]azepine, 5,8-dihydro-6H-pyrano[3,4-b]pyridine, 5,6-dihydro-[1,4]dioxino[2,3-d]thiazole, 6,7-dihydro-5H-pyrrolo[1,2-c]imidazole;

Phenyl-Phenyl:
Naphthyl;

Phenyl-heteroaryl:
Benzofuran, isoquinoline, benzo[d]isoxazole, 1H-benzotriazole, benzothiazole;

Heteroaryl-heteroaryl:
Thiazolo[4,5-c]pyridine, thieno[2,3-d]isoxazole, [1,6]naphthyridine, imidazo[1,2-a]pyridine, furo[2,3-b]pyridine.

Preferred examples of condensed radicals are naphtyl or indanyl. All these examples may be substituted as mentioned above.

The terms cycloalkyl, heterocyclyl, phenyl or heteroaryl are used here interchangeable for being either directly attached as a substituent or being the condensed radical.

In a further embodiment of the compounds of formula I
B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)-C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—; —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)-C(R15R16)- or —O—C(R13R14)-C(R13R14)-O—C(R13R14)-;

with the proviso that, if A is connected to the linker B via a nitrogen atom being part of A, the atom of the linker which is connected to A is a carbon atom;

R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19
is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

R44, R45 and R46
are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms;

y is 0, 1 or 2.

In a preferred embodiment of a compound of formula I
B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is H or alkyl having 1, 2, 3, 4, 5 or 6 carbon atoms.

In a more preferred embodiment of a compound of formula I

B is —C(R11R12)-C(R13R14)-O—, —C(R11R12)-C(R15R16)-C(R13R14)-O—, —O—C(R13R14)-C(R13R14)-O—, —C(R17)=C(R18)-C(R13R14)-O—, —C≡C—C(R13R14)-O—, —C(R11R12)-C(R13R14)-C≡C—, —O—C(R13R14)-C≡C—, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker via a nitrogen atom being part of A, the atom of the linker which is connected to A is a carbon atom;

R11 and R12
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14 R17 and R18
are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16
are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms.

In an even more preferred embodiment of a compound of formula I

B is —C(R11R12)-C(R13R14)-O—, —C(R11R12)-C(R15R16)-C(R13R14)-O—, —O—C(R13R14)-C(R13R14)-O—, —C(R11R12)-C(R15R16)-C(R15R16)-C(R13R14)-O—, —O—C(R13R14)-C(R15R16)-C(R13R14)-O—, or —C(R13R14)-O—C(R13R14)-C(R13R14)-O—, with the proviso that, if A is connected to the linker B via a nitrogen atom being part of A, the atom of the linker which is connected to A is a carbon atom;
wherein R11-R16 are, independently of each other, hydrogen, F or alkyl having 1, 2, 3, 4 carbon atoms, preferably alkyl being methyl, more preferably R11-R16 are hydrogen or methyl, preferably hydrogen.

In an even more preferred embodiment

B is —C(R11R12)-C(R13R14)-O—, —O—C(R13R14)-C(R13R14)-O—, —C(R11R12)-C(R15R16)-C(R15R16)-C(R13R14)-O or —O—C(R13R14)-C(R15R16)-C(R13R14)-O—;

with the proviso that, if A is connected to the linker B via a nitrogen atom being part of A, the atom of the linker which is connected to A is a carbon atom;
wherein R11-R16 are, independently of each other, hydrogen, F or alkyl having 1, 2, 3, 4 carbon atoms, preferably alkyl being methyl, more preferably R11-R16 are hydrogen or methyl, preferably hydrogen.

Within the embodiments of B those are preferred, wherein R11-R18 are, independently of each other, hydrogen, F or alkyl having 1, 2, 3, 4 carbon atoms, preferably alkyl being methyl, more preferably R11-R18 are hydrogen or methyl, preferably hydrogen.

Also, within the embodiments of B those are preferred, wherein R19 is hydrogen or methyl, preferably hydrogen.

Also, within the embodiments of B those are preferred, wherein y is 0.

In a more preferred embodiment of B, R11-R19 are, independently of each other, hydrogen or methyl, preferably hydrogen.

Linker B is attached with its left hand side to the residue A and with its right hand side to the ring system.

In a further embodiment of compounds of formula I
R1 is hydrogen or alkyl having 1, 2, 3, 4, 5 or 6 carbon atoms which can be unsubstituted or substituted by 1, 2, 3, 4 or 5 radicals selected from the group consisting of F, Cl, Br, I, —$O_i$—$(CH_2)_j$—R25;
i is 0 or 1;
j is 0, 1, 2 or 3;

R25 is hydrogen or phenyl, heteroaryl having 5 or 6 atoms, cycloalkyl having 3, 4, 5 or 6 carbon atoms or heterocyclyl having 3, 4 5, 6, 7 or 8 atoms;
preferably, R1 is not hydrogen;
and
R2 is alkyl having 1, 2, 3, 4, 5 or 6 carbon atoms or phenyl,
wherein alkyl is unsubstituted or substituted by 1, 2, 3, 4 or 5 radicals selected from the group consisting of F, Cl, Br, I, —O$_m$—(CH$_2$)$_n$—R26;
m is 0, or 1;
n is 0, 1, 2 or 3;
R26 is hydrogen, phenyl, heteroaryl having 5 or 6 atoms, ccycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2, or 3 radicals selected from F, Cl, Br or I;
and wherein phenyl is unsubstituted or substituted by 1, 2, 3, 4 or 5 radicals selected from the group consisting of F, Cl, Br, I, OH, CN, NO$_2$, SCF$_3$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
or, in another embodiment,
R1 and R2
form, together with the carbon atom to which they are attached, a 3-, 4-, 5- or 6-membered saturated or partly saturated carbon ring, which can be condensed to phenyl;
preferably, the formed ring is not condensed;
wherein the formed ring and the optionally condensed phenyl can be unsubstituted or substituted by 1, 2, 3, 4 or 5 radicals selected from the group consisting of F, Cl, Br, I, CN, NO$_2$, SCF$_3$, SF$_5$, or alkyl having 1, 2, 3 or 4 carbon atoms;
or, in another embodiment,
R1 and R2
form, together with the carbon atom to which they are attached, a 4-, 5- or 6-membered saturated or partly saturated carbon ring, wherein one carbon atom, which is not adjacent to the carbon atom to which R1 and R2 are attached, is replaced by —O—, —NR58- or —S(O)$_w$—, and in which the formed ring can optionally be condensed to phenyl; preferably the formed ring is not condensed;
wherein the formed ring and the optionally condensed phenyl can be unsubstituted or substituted by 1, 2, 3, 4 or 5 radicals selected from the group consisting of F, Cl, Br, I, CN, NO$_2$, SCF$_3$, SF$_5$, or alkyl having 1, 2, 3 or 4 carbon atoms;
R58 is hydrogen, alkyl having 1, 2, 3 or 4 carbon atoms or C(O)R58;
R59 is hydrogen, alkyl with 1, 2, 3 or 4 carbon atoms or phenyl;
preferably, R58 is hydrogen or alkyl having 1, 2, 3 or 4 carbon atoms;
w is 0, 1 or 2;
preferably w is 0.
In a preferred embodiment of compounds of formula I
R1 is hydrogen or alkyl having 1, 2, 3, 4, 5 or 6 carbon atoms;
preferably, R1 is alkyl having 1, 2, 3, 4, 5 or 6 carbon atoms;
and
R2 is alkyl having 1, 2, 3, 4, 5 or 6 carbon atoms or phenyl;
wherein alkyl is unsubstituted or substituted by 1, 2, 3, 4 or 5 radicals selected from the group consisting of F, Cl, Br, I, —O$_m$—(CH$_2$)$_n$—R26;
m is 0, or 1;
n is 0, 1, 2 or 3;

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2, or 3 radicals selected from F, Cl, Br or I;
preferably, R26 is hydrogen or phenyl;
or, in another preferred embodiment,
R1 and R2
form, together with the carbon atom to which they are attached, a 3-, 4, 5- or 6-membered saturated or partly saturated carbon ring, which can be condensed to phenyl;
preferably the ring is not condensed;
or, in another preferred embodiment,
R1 and R2
form, together with the carbon atom to which they are attached, a 4-, 5- or 6-membered saturated or partly saturated carbon ring, wherein one carbon atom, which is not adjacent to the carbon atom to which R1 and R2 are attached, is replaced by —O—, —NH— or —S —;
preferably the ring is saturated, and preferably one carbon atom, which is not adjacent to the carbon atom to which R1 and R2 are attached, is replaced by —O— or —S—.
In a more preferred embodiment
R1 is alkyl having 1, 2, 3 or 4 carbon atoms;
and
R2 is alkyl having 1, 2, 3 or 4 carbon atoms, phenyl or benzyl;
or, in another more preferred embodiment,
R1 and R2
form, together with the carbon atom to which they are attached, a cyclopropane, cyclobutane, cyclopentane, cyclohexane, cyclopentene ring or indene;
preferably R1 and R2 form a cyclopropane, cyclobutane, cyclopentane, cyclohexane or cyclopentene ring;
or, in another more preferred embodiment,
R1 and R2
form, together with the carbon atom to which they are attached, a tetrahydro-thiophene or tetrahydro-thiopyrane ring.
In an even more preferred embodiment
R1 is methyl or ethyl;
more preferably, methyl;
and
R2 is methyl or ethyl
or, in another even more preferred embodiment,
R1 and R2
form, together with the carbon atom to which they are attached, a cyclobutane or cyclopentane ring.
In a most preferred embodiment
R1 is methyl;
and
R2 is methyl or ethyl;
more preferably, methyl.
In given embodiments of the present invention one or more or all of the groups contained in the compounds of formula I can independently of each other have any of the given, preferred, more preferred or most preferred definitions of the groups specified above or any one or some of the specific denotations which are comprised by the definitions of the groups and specified above, all combinations of given or preferred definitions, more preferred or most preferred and/or specific denotations being a subject of the present invention.
Special preference is given to the following compounds of the formula I, selected from the group consisting of
2-Methyl-2-[(1-phenethyloxy-5,6,7,8-tetrahydro-naphthalene-2-carbonyl)-amino]-propionic acid;

2-{[1-(2-Cyclohexyl-ethoxy)-5,6,7,8-tetrahydro-naphthalene-2-carbonyl]-amino}-2-methyl-propionic acid;
2-Methyl-2-{[1-(2-phenoxy-ethoxy)-5,6,7,8-tetrahydro-naphthalene-2-carbonyl]-amino}-propionic acid;
2-({1-[2-(4-Fluoro-phenoxy)-ethoxy]-5,6,7,8-tetrahydro-naphthalene-2-carbonyl}-amino)-2-methyl-propionic acid;
2-Methyl-2-{[1-(4-phenyl-butoxy)-5,6,7,8-tetrahydro-naphthalene-2-carbonyl]-amino}-propionic acid;
2-Methyl-2-{[1-(2-thiophen-2-yl-ethoxy)-5,6,7,8-tetrahydro-naphthalene-2-carbonyl]-amino}-propionic acid;
2-Methyl-2-{[1-(3-phenoxy-propoxy)-5,6,7,8-tetrahydro-naphthalene-2-carbonyl]-amino}-propionic acid;
2-Methyl-2-{[7-(3-phenyl-propoxy)-benzo[b]thiophene-6-carbonyl]-amino}-propionic acid;
2-Methyl-2-[(7-phenethyloxy-benzo[b]thiophene-6-carbonyl)-amino]-propionic acid;
2-Methyl-2-{[7-(2-phenoxy-ethoxy)-benzo[b]thiophene-6-carbonyl]-amino}-propionic acid;
2-({7-[2-(4-Fluoro-phenoxy)-ethoxy]-benzo[b]thiophene-6-carbonyl}-amino)-2-methyl-propionic acid or
2-Methyl-2-{[4-(2-phenoxy-ethoxy)-benzo[b]thiophene-5-carbonyl]-amino}-propionic acid
and/or a pharmaceutically acceptable salt and/or a prodrug thereof.

The compounds of the formula I can be present in the form of their salts. An overview of pharmaceutically employed salts can be found in the "Handbook of Pharmaceutical Salts", edited by P. Heinrich Stahl, Camille G. Wermuth, Verlag Helvetica Chimica Acta, Switzerland, 2002. Suitable base addition salts are salts of all pharmacologically acceptable bases, for example alkali metal, earth alkali metal or metal salts, preferably sodium, potassium, magnesium, calcium or zink salts, or as ammonium salts, for example as salts with ammonia or organic amines or amino acids, preferably as salts formed with ammonia, arginine, benethamine, benzathine, choline, deanol, diethanolamine, diethylamine, 2-(diethylamino)-ethanol, ethanolamine, ethylendiamine, N-methyl-glucamine, hydrabamine, 1H-imidazole, lysine, 4-(2-hydroxyethyl)-morpholine, piperazine, 1-(2-hydroxyethyl)-pyrrolidine, triethanolamine or tromethamine; If the compounds contain a basic group, they are capable of forming salts with acid, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerolphosphates, maleates, benzoates, oxalates and pamoates. This group also corresponds to the physiologically acceptable anions; but also trifluoroacetates. They can also be present as zwitterions.

If the inventive compounds contain one or more centers of asymmetry, these may independently of one another have the S and the R configuration. The compounds may be in the form of optical isomers, of diastereomers, of racemates or of mixtures thereof in any ratio.

The compounds of the formula I according to the invention can contain mobile hydrogen atoms, that is be present in various tautomeric forms. The present invention relates to all the tautomers of the compounds of the formula I.

The present invention furthermore encompasses derivatives of compounds of the formula I, for example solvates, such as hydrates and adducts with alcohols, esters, prodrugs and other physiologically tolerated derivatives of compounds of the formula I, and also active metabolites of compounds of the formula I. Further the invention contains all crystal modifications of compounds of formula I.

The invention relates, in particular, to prodrugs of the compounds of the formula I which are not necessarily pharmacologically active in vitro but which are converted in vivo, under physiological conditions, into active compounds of the formula I, for example by hydrolysis in blood. The skilled person is familiar with suitable prodrugs for the compounds of the formula I, that is chemically modified derivatives of the compounds of the formula I possessing properties which have been improved in a desired manner. Further details with regard to prodrugs can be found, for example, in Fleisher et al., Advanced Drug Delivery Reviews 19 (1996) 115-130; Design of Prodrugs, H. Bundgaard, Ed., Elsevier, 1985; or H. Bundgaard, Drugs of the Future 16 (1991) 443. Prodrugs which are especially suitable for the compounds of the formula I are ester prodrugs of carboxylic acid groups, amide prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom which is located on a nitrogen atom is replaced with an acyl group or carbamate group. Examples of ester prodrugs and amide prodrugs which may be prepared from the carboxylic acid group in a compound of formula I and which may be mentioned are ($C_1$-$C_4$)-alkyl esters such as methyl esters, ethyl esters, n-propyl esters, isopropyl esters, n-butyl esters and isobutyl esters, substituted alkyl esters such as hydroxyalkyl esters, acyloxyalkyl esters, aminoalkyl esters, acylaminoalkyl esters and dialkylaminoalkyl esters, unsubstituted amides and N—($C_1$-$C_4$)-alkylamides, such as methylamides or ethylamides. For example the methyl and ethyl esters of the compounds listed above are included.

Alkyl radicals are linear, ie. a straight-chain, or branched hydrocarbons, which, where indicated, contain a specified number of carbon atoms, e.g. 1, 2, 3 or 4 atoms, 1, 2, 3, 4, 5 or 6 atoms or 1, 2, 3, 4, 5, 6, 7 or 8 atoms. This also applies if they carry substituents or occur as substituents of other radicals, for example in alkoxy, arylalkyl, heteroarylalkyl, fluoroalkyl or —S-alkyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. Where indicated one or more, for example 1, 2, 3, 4, 5, 6, 7, 8, 9, 10, 11, 12 or 13, hydrogen atoms in alkyl radicals may be replaced by fluorine atoms to form fluoroalkyl radicals. Examples of such radicals are difluoromethyl, trifluoromethyl, pentafluoroethyl, 2,2,2-trifluoroethyl; 3,3,3-trifluoropropyl; 3,3,3-trifluorobutyl or 4,4,4-trifluorbutyl.

Cycloalkyl radicals are hydrocarbon rings, which, where indicated, contain a specified number of carbon atoms, for example 3, 4, 5 or 6 carbon atoms or 3, 4, 5, 6, 7 or 8 carbon atoms. Examples of cycloalkyl groups are cyclopropyl, cyclobutyl, cyclopentyl, cyclohexyl, cycloheptyl or cyclooctyl. Cycloalkyl radicals may be unsubstituted or be substituted one or more times, for example once, twice or three times, by identical or different specified radicals in identical or different positions. Cycloalkyl radicals can be saturated or partly unsaturated (contain double bonds). For example a cycloalkyl radical may contain zero, one or two double bonds. This also applies if they carry substituents or occur as substituents of other radicals, for example in the radical cycloalkylalkyl. Where indicated, a cycloalkyl radical may be condensed to a cycloalkyl, aryl, heterocyclyl or heteroaryl radical. Where for a cycloalkylalkyl or cycloalkylalkoxy radical the number of carbon atoms has been given, this is the sum of the number of the carbon atoms in the cycloalkyl and in the alkyl or alkoxy radical, respectively.

Heterocyclyl radicals or heterocycle radicals are hydrocarbon ring compounds, which where indicated, contain a specified number of carbon atoms, for example 3, 4, 5, 6, 7 or 8 atoms or 5, 6, 7 or 8 atoms, respectively, in which one or more ring atoms are replaced by oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. Heterocyclyl radicals can be saturated or partly unsaturated (contain double bonds). For example a heterocyclyl radical may contain zero, one or two double bonds.

The heterocyclyl radicals may be attached at all positions, for example at the 1 position, 2 position, 3 position, 4 position, 5 position, 6 position, 7 position or 8 position. Heterocycle radicals may be unsubstituted or be substituted one or more times, for example once, twice or three times, by identical or different specified radicals in identical or different positions. Substitutions can occur on free carbon atoms or on nitrogen atoms. Examples of heterocycles are oxirane, aziridine, tetrahydrofurane, tetrahydropyrane, dioxolane, for example 1,3-dioxolane, dioxane, for example 1,4-dioxan, piperidine, pyrrolidin, imidazolidine, triazolidine, hexahydropyrimidine, piperazine, tetrahydropyridazine, triazinane, for example, 1,3,5-triazinane, 1,2,3-triazinane or 1,2,4-triazinane, tetrahydrothiophene, tetrahydrothiopyrane, dithiolane, for example 1,3-dithiolane, dithiane, thiazolidine, oxazolidine, oxathiolane, for example 1,3-oxathiolane, morpholine or thiomorpholine. Where indicated, the heterocyclyl radical may be condensed to a cycloalkyl, heterocyclyl or heteroaryl.

The term "aryl" means phenyl, 1-naphthyl, 2-naphthyl and indenyl. The aryl radical may be unsubstituted or be substituted one or more times, for example once, twice, three or four times, by identical or different specified radicals. If an aryl radical is substituted, it preferably has one, two or three identical or different substituents. This likewise applies to substituted aryl radicals in groups such as arylalky. Where indicated, aryl radicals may be condensed to e.g. a cycloalkyl or heterocyclyl radical.

"Heteroaryl" radicals are aromatic 5 or 6-membered carbon ring compounds, in which one or more ring atoms are replaced by oxygen atoms, sulfur atoms or nitrogen atoms, e.g. 1, 2, 3 or 4 nitrogen atoms, 1 oxygen atom, 1 sulfur atom or a combination of various heteroatoms. The heteroaryl radicals may be attached by all positions, for example at the 1 position, 2 position, 3 position, 4 position, 5 position or 6 position. Heteroaryls may be unsubstituted or substituted one or more times, for example once, twice, three or four times, by identical or different specified radicals. This applies likewise to heteroaryl radicals such as, for example, in the radical heteroarylalkyl. Examples of heteroaryls are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl or tetrazolyl, in particular pyridyl, thienyl or imidazolyl. Pyridyl stands both for 2-, 3- and 4-pyridyl, Thienyl stands both for 2- and 3-thienyl. Where indicated, a heteroaryl radical may be condensed to e.g. a cycloalkyl or heterocyclyl radical.

When any variable (e.g. aryl, R1) occurs more than one time in any constituent, its definition on each occurrence is independent of its definition at every other occurrence. Also, combinations of substituents and/or variables are permissible only if such combinations result in stable compounds.

The invention further relates to the following processes for preparing the compounds of the formula I.

Compounds of formula I, wherein the atom in B linked to the ring system is oxygen, can be prepared as described in Scheme 1

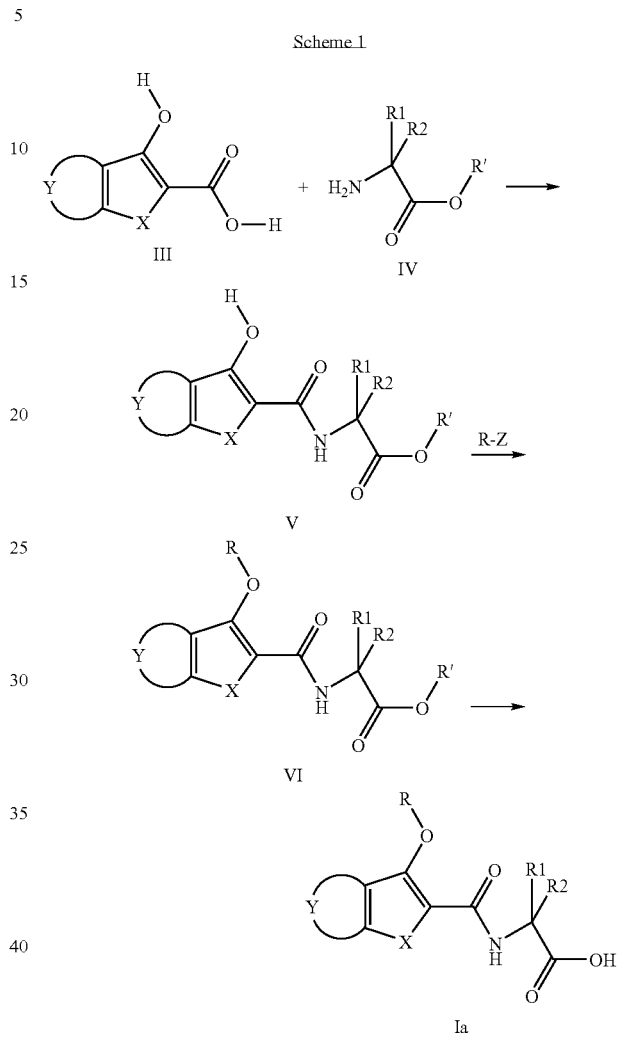

which comprises
a) coupling of an acid of formula III with an amino compound of formula IV to an amide of formula V,
b) reacting a compound of formula V with a reagent R—U to an compound of formula VI,
c) converting an ester of formula VI to an acid of formula Ia wherein in the compounds of the formulae Ia, III, IV, V and VI X, Y, R1 and R2 are defined as in formula I,
R' is alkyl having 1, 2, 3, 4, 5 or 6 carbon atoms,
R—U is A-B1-L or A-B1-OH and R— is A-B1-,
wherein A is defined as in formula I and —B1- is defined in a manner so that —B1-O— is contained in the definition of B as given in formula I;
U is OH or L, wherein L is a leaving group, which can undergo nucleophilic substitution with an amine.

The procedure for preparing the compounds of the formula I is initially a coupling of an amino compound of formula IV with an acid of formula III for preparing the compound of formula V generally in the presence of an coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula V to the compound of formula VI can be achieved by adding the reagent R-L (U=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively the reaction of the compound of formula V with R—OH (U=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range.

The cleavage of the ester of formula VI to the acid of formula Ia can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds VI or Ia in Scheme 1, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively compounds of formula I, wherein the atom in B linked to the ring system is oxygen, can be prepared as described in Scheme 2

Scheme 2

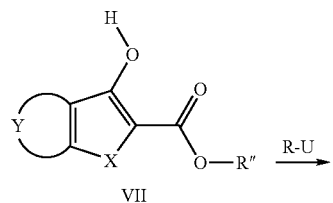

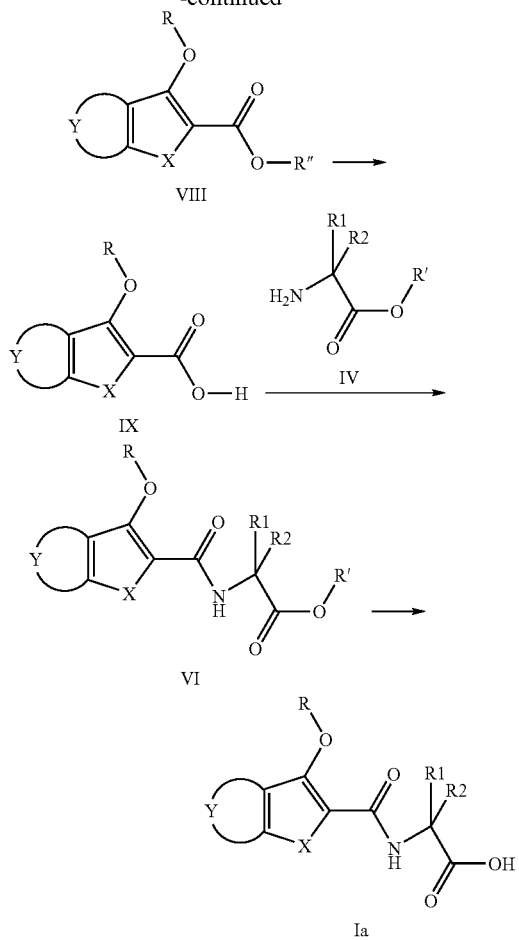

which comprises
a) reacting a compound of formula VII with an reagent R—U to a compound of formula VIII
b) converting an ester of formula VIII to an acid of formula IX
c) coupling of an acid of formula IX with an amino compound of formula IV to an amide of formula VI
d) converting an ester of formula VI to an acid of formula Ia wherein in the compounds of the formulae Ia, IV, VI, VII, VIII and IX
X, Y, R1 and R2 are defined as in formula I,
R' is alkyl having 1, 2, 3, 4, 5 or 6 carbon atoms,
R" is alkyl having 1, 2, 3, 4, 5 or 6 carbon atoms or aryl,
R-Z is A-B1-L or A-B1-OH and R— is A-B1-,
  wherein A is defined as in formula I and —B1- is defined in a manner so that —B1-O— is contained in the definition of B as given in formula I;
U is OH or L, wherein L is a leaving group, which can undergo nucleophilic substitution with an amine.

The procedure for preparing the compounds of the formula I is initially a transformation of the compound of formula VII to the compound of formula VIII which can be achieved by adding the reagent R-L (U=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h depending on the composition of the mixture and the chosen temperature range Alternatively, the reaction of the compound of formula VII with R—OH (U=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80, more preferably from 0° C. to 25° C. The reaction time is generally from 15 min to 6 days, preferably from 15 min to 16 h, depending on the composition of the mixture and the chosen temperature range.

The subsequent cleavage of the ester of formula VIII to the acid of formula IX can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

The resulting compound of formula IX can be coupled with the amino compound of formula IV to form the compound of formula VI generally in the presence of an coupling agent, for example EDC, DIC or HATU and optionally an additional base, for example triethylamine or Hünig's base, in an appropriate solvent, in particular in an aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

The cleavage of the ester of formula VI to the acid of formula Ia in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range. Optionally, compounds Ia, VI, VII or IX in Scheme 2, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively, compounds of formula I, wherein the atom in B linked to the ring system is —N(R19)- or a carbon atom, can be prepared as described in Scheme 3

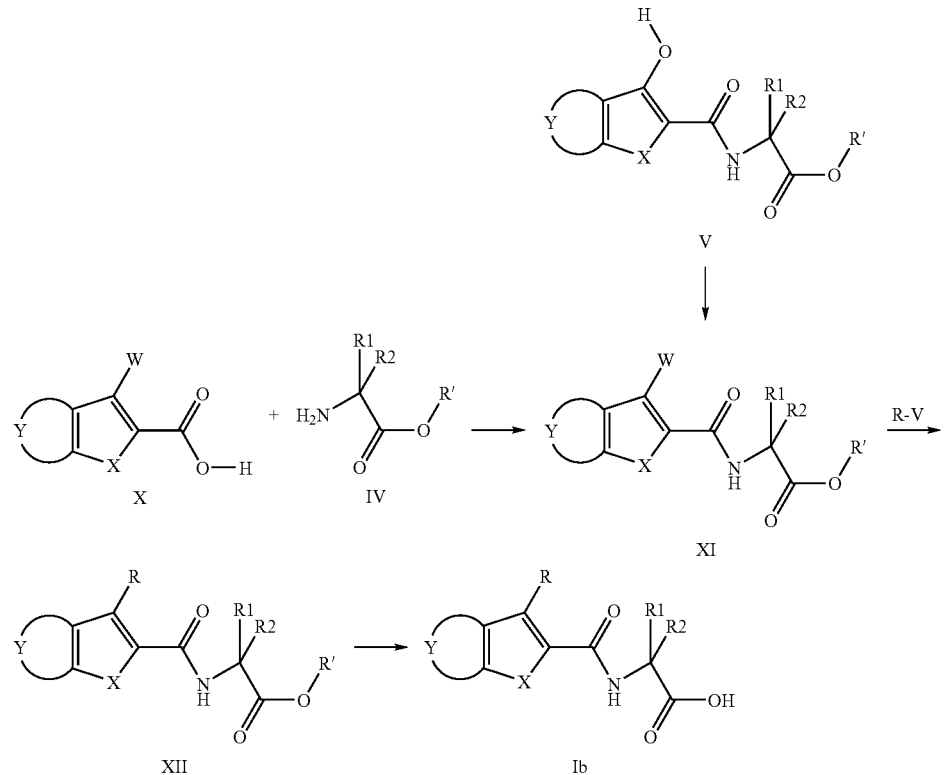

Scheme 3 which comprises
a) coupling of an acid of formula X with an amino compound of formula IV to an amide of formula XI, or, alternatively, the conversion of a compound of formula V to a compound of formula XI (if W is triflate, mesylate or tosylate), b) reacting a compound of formula XI with an reagent R—V to an compound of formula XII, c) converting an ester of formula XII to an acid of formula Ib wherein in the compounds of the formulae Ib, IV, V, X, XI and XII X, Y, R1 and R2 are defined as in formula I, W is halogen, for example I, Br or Cl, or triflate, mesylate or tosylate, R' is alkyl having 1, 2, 3, 4, 5 or 6 carbon atoms, R—V is A-B2-NR19-H and R— is A-B2-NR19-or R—V is A-B3-CR17=CR18-H and R— is A-B3-CR17=CR18-or R—V is A-B3-CR17=CR18-B(OR''')$_2$ and R— is A-B3-CR17=CR18-or R—V is A-B3-CR17=CR18-Sn(R''')$_3$ and R is A-B3-CR17=CR18-or R—V is A-B3-CR17=CR18-ZnHal and R— is A-B3-CR17=CR18-or R—V is A-B4-C≡C—H and R— is A-B4-C≡C—, wherein A is defined as in formula I, —B2- is defined in a manner so that —B2-NR19- is contained in the definition of B as given in formula I, —B3- is defined in a manner, so that —B3-CR17=CR18- is contained in the definition of B as given in formula I, —B4- is defined in a manner, so that —B4-C≡C— is contained in the definition of B as given in formula I, R17 and R18 are substituents at a carbon atom being part of a double bond as defined for B in formula I and R19 is defined as in formula I, R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups, R''' is alkyl having 1, 2, 3, 4, 5 or 6 carbon atoms, Hal is halogen, for example 1, Br or Cl.

The procedure for preparing the compounds of the formula I is initially a coupling of an amino compound of formula IV with an acid of formula X for preparing the compound of formula XI generally in the presence of a coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Alternatively, a compound of formula V can be converted into a compound of formula XI, in which W is defined as triflate, tosylate or mesylate, by reacting it with an anhydride or chloride of trifluoromethane sulfonic acid, para-toluene sulfonic acid or methyl sulfonic acid in the presence of a suitable base, for example triethylamine in an appropriate solvent, for example dichloromethane. The reaction temperature in this case is generally from −80° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula XI to the compound of formula XII can be achieved by reacting with a reagent R—V, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The cleavage of the ester of formula XII to the acid of formula Ib can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds Ib or XII in Scheme 3, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Alternatively compounds of formula I, wherein the atom in B linked to the ring system is —N(R19)- or a carbon atom, can be prepared as described in Scheme 4

Scheme 4

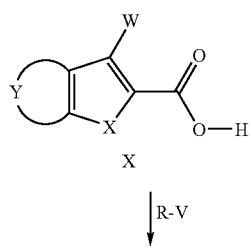

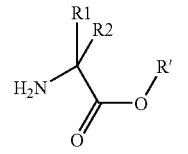

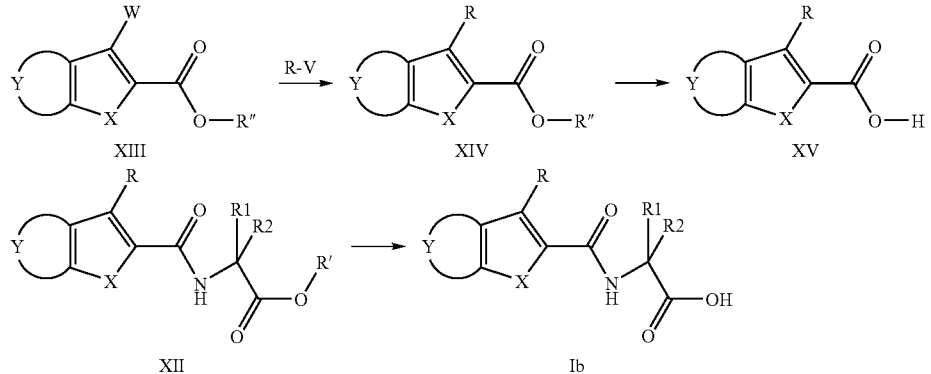

which comprises
a) reacting a compound of formula XIII with a reagent R—V to a compound of formula XIV
b) converting an ester of formula XIV to an acid of formula XV or, alternatively, reacting a compound of formula X with a reagent R—V to a compound of formula XV
c) coupling of an acid of formula XV with an amino compound of formula IV to an amide of formula XII
d) converting an ester of formula XII to an acid of formula Ib
wherein in the compounds of the formulae Ib, IV, X, XII, XIII, XIV and XV
X, Y, R1 and R2 are defined as in formula I,
W is halogen, for example I, Br or Cl, or triflate, mesylate or tosylate,
R' is alkyl having 1, 2, 3, 4, 5 or 6 carbon atoms,
R'' is alkyl having 1, 2, 3, 4, 5 or 6 carbon atoms or aryl,
R—V is A-B2-NR19-H and R— is A-B2-NR19-or
R—V is A-B3-CR17=CR18-H and R— is A-B3-CR17=CR18-or
R—V is A-B3-CR17=CR18-B(OR''')$_2$ and R— is A-B3-CR17=CR18-or
R—V is A-B3-CR17=CR18-Sn(R'''')$_3$ and R is A-B3-CR17=CR18-or
R—V is A-B3-CR17=CR18-ZnHal and R— is A-B3-CR17=CR18-or
R—V is A-B4-C≡C—H and R— is A-B4-C≡C—,
wherein
A is defined as in formula I,
—B2- is defined in a manner so that —B2-NR19- is contained in the definition of B as given in formula I,
—B3- is defined in a manner, so that —B3-CR17=CR18- is contained in the definition of B as given in formula I,
—B4 is defined in a manner, so that —B4-C≡C— is contained in the definition of B as given in formula I,
R17, R18 are substituents at a carbon atom being part of a double bond as defined for B in formula I and R19 is defined as in formula I,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups, R'''' is alkyl having 1, 2, 3, 4, 5 or 6 carbon atoms,
Hal is halogen, for example I, Br or Cl.

The procedure for preparing the compounds of the formula I is initially a transformation of the compound of formula XIII to the compound of formula XIV which can be achieved by reacting with a reagent R—V, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The subsequent cleavage of the ester of formula XIV to the acid of formula XV can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

Alternatively, a transformation of a compound of formula X to the compound of formula XV can be achieved by reacting with a reagent R—V, often under inert conditions and in an appropriate solvent, in the presence of a suitable catalytic system, which can contain a palladium and/or copper complex and/or salt, for example Pd$_2$ dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 250°, more preferably from 20° C. to 200° C. The reaction time is generally from 15 min to 6 days, preferably from 15 min to 16 h, depending on the composition of the mixture and the chosen temperature range.

The resulting compound of formula XV can be coupled with the amino compound of formula IV to form the compound of formula XII generally in the presence of a coupling agent, for example EDC, DIC or HATU and optionally an additional base, for example triethylamine or Hünig's base, in an appropriate solvent, in particular in aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The cleavage of the ester of formula XII to the acid of formula Ib in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

Optionally, compounds Ib, XII, XIV or XV in Scheme 4, which contain within R triple bonds or non-aromatic double bonds, can be (partially) reduced, so that triple bonds are converted to double bonds, or so that triple bonds are converted to single bonds, or so that non-aromatic double bonds are converted to single bonds, or so that triple bonds and non-aromatic double bonds are converted to single bonds. These transformations can be carried out in analogy to the processes which are described in the literature and are known to those skilled in the art, for example by (partial) hydrogenation of said compounds in the presence of homogenous or heterogenous catalysts.

Compounds of formula I can be prepared as described in Scheme 5

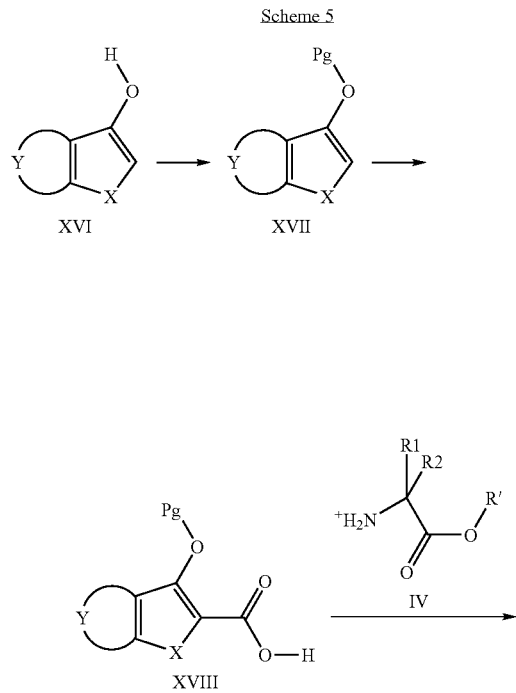

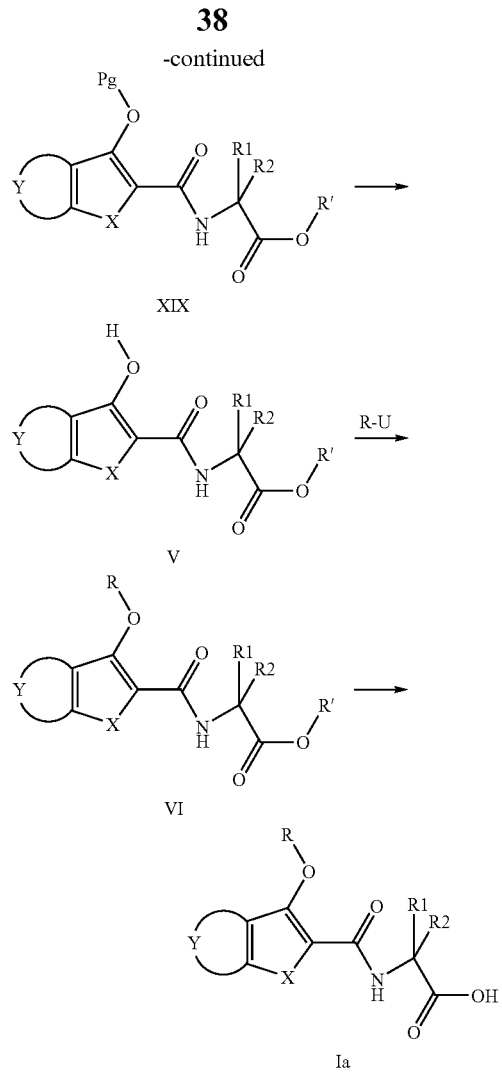

which comprises
a) protecting the hydroxy group in a compound of formula XVI to obtain a compound of formula XVII
b) introducing a carboxy group in ortho-position to the protected hydroxy group in a compound XVII to obtain an acid of formula XVIII
c) coupling of an acid of formula XVIII with an amino compound of formula IV to an amide of formula XIX,
d) deprotecting the hydroxy group in a compound of formula XIX to obtain a compound of formula V
e) reacting a compound of formula V with a reagent R-Z to a compound of formula VI,
f) converting an ester of formula VI to an acid of formula Ia
wherein in the compounds of the formulae Ia, IV, V, VI, XVI, XVII, XVII and XIX
X, Y, R1 and R2 are defined as in formula I,
R' is alkyl having 1, 2, 3, 4, 5 or 6 carbon atoms,
R—U is A-B1-L or A-B1-OH and R— is A-B1-,
wherein A is defined as in formula I and —B1- is defined in a manner so that —B1-O— is contained in the definition of B as given in formula I;
U is OH or L, wherein L is a leaving group, which can undergo nucleophilic substitution with an amine.

Pg is a protecting group for (aromatic) hydroxy functions, which has an ortho-directing effect in a metalation reaction, for example a lithiation, and which can be cleaved in the presence of a primary or secondary alkyl ester and an amide, for example Pg is a methoxymethyl group.

The procedure for preparing the compounds of the formula I is initially a protection of a hydroxy group of the compound of formula XVI with a protecting group Pg, which has an ortho-directing effect in a metalation reaction, for example a lithiation, and which can be cleaved in the presence of a primary or secondary alkyl ester and an amide, for example Pg is a methoxymethyl group. The protection of a compound of formula XVI to the compound of formula XVII can be achieved by adding, for example methoxymethylchloride or -bromide in the presence of a suitable base, for example sodium hydride in a suitable solvent, for example DMF or THF. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Subsequently, the transformation of the compound of formula XVII to the compound of formula XVIII can be achieved by a metallation ortho to the hydroxy group protected with an ortho-directing protecting group and a carboxylation; this can be achieved by reacting the compound of formula XVII in a suitable solvent, for example diethyl ether or THF, with a metallation reagent, for example a lithiation reagent as n-butyllithium, sec-butyllithium or tert-butyllithium, optionally in the presence of a chelating agent, such as, for example, N,N,N',N'-tetramethylethylenediamine and subsequently, for example, with carbon dioxide. The reaction temperature in this case is generally from −100° C. to 150° C., preferably from −80° C. to 100°, more preferably from −80° C. to 20° C. The reaction time is generally from 15 min to 6 days, preferably from 15 min to 16 h depending on the composition of the mixture and the chosen temperature range. The next transformation is a coupling of an amino compound of formula IV with an acid of formula XVIII for preparing the compound of formula XIX generally in the presence of an coupling agent, for example EDC, DIC or HATU and optionally an additional base, for example triethylamine or Hünig's base, in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range. The subsequent transformation is a cleavage of the ortho directing protecting group Pg of the compound of formula XIX to the compound or formula V. This can be achieved, for example in the case, where Pg is a methoxymethyl group by reacting the compound of formula XIX in the presence of an acid, for example hydrochloric acid, in a suitable solvent as for example, THF and isopropanol. The reaction temperature in this case is generally from 0° C. to 200° C., preferably from 20° C. to 80° C. The reaction time is generally from 2 min to 6 days, preferably from 2 min to 16 h, depending on the composition of the mixture and the chosen temperature range. Subsequently, the transformation of the compound of formula V to the compound of formula VI can be achieved by adding the reagent R-L (U=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively, the reaction of the compound of formula V with R—OH (U=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range. The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

The compounds of formula Ia and Ib are contained in the compound of formula I.

The starting compounds of the formulae III, IV, V, VII, X, XIII and XVI are commercially available or can be prepared by a skilled artisan according to procedures described in the literature.

The workup and optionally the purification of the products and/or intermediates are effected by the customary methods such as extraction, chromatography or crystallization and the customary dryings.

Alternative processes for preparing the compounds are described in the examples and are also part of the invention.

Functional groups in the starting compounds may be present in protected form or in the form of precursors, and then be converted into the desired groups in the compounds of the formula I prepared by the process described above. Corresponding protective group techniques are known to the skilled artisan.

It is likewise possible for appropriate functional groups to be derivatized by methods known to the skilled artisan.

Another aspect of the invention is the use of a compound of the formula I and/or a pharmaceutically acceptable salt and/or a prodrug thereof alone or in combination with other medicaments or active ingredients as for producing a medicament for the treatment or prophylaxis of chemokine mediated diseases.

The invention further relates to the use of a compound of the formula I and/or a pharmaceutically acceptable salt and/or a prodrug thereof alone or in combination with other medicaments or active ingredients as for producing a medicament for the treatment or prophylaxis of a chemokine mediated disease, wherein the chemokine binds to a CXC receptor.

Another aspect of the invention is the use of a compound of the formula I and/or the pharmaceutically acceptable salt and/or a prodrug thereof alone or in combination with other medicaments or active ingredients as for producing a medicament for the treatment or prophylaxis of a chemokine mediated disease, wherein the chemokine binds to a CXCR2 and/or CXCR1 receptor, in particular to a CXCR2 receptor.

The invention further relates to the use of a compound of the formula I and/or a pharmaceutically acceptable salt and/or a prodrug thereof alone or in combination with other medicaments or active ingredients as for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgerical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multiorgan dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer. In particular, a compound of formula I is used alone.

As a further aspect of the present invention, certain compounds of formula I may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

Also claimed is a medicine or pharmaceutical composition for human or veterinary use, comprising an effective amount of a compound of the formula I and/or a pharmaceutically acceptable salt and/or a prodrug thereof, together with pharmaceutically acceptable carriers and additives, alone or in combination with other active pharmaceutical ingredients or medicaments.

Medicaments which comprise a compound of the formula I and/or a pharmaceutically acceptable salt and/or a prodrug thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or a pharmaceutically acceptable salt and/or a prodrug thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or a pharmaceutically acceptable salt and/or a prodrug thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or a pharmaceutically acceptable salt and/or a prodrug thereof for a patient weighing about 75 kg is at least 0.001 mg/kg, preferably 0.01 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

List of Abbreviations:
O-(7-Azabenzotriazol-1-yl)-N,N,N',N'-tetramethyluronium Hexafluorophosphate HATU
[2-(1H)-benzotriazol-1-yl]-1,1,3,3-tetramethyluronium tetra-fluoroborate TBTU
N-Brom-succinimide NBS
Dichloromethane DCM
4-Dimethylaminopyridine DMAP
Diethylazodicarboxylate DEAD
Diisoppropylazodicarboxylate DIAD
N,N'-Diisopropylcarbodiimid DIC
1-(3-Dimethylaminopropyl)-3-ethylcarbodiimide-Hydrochloride EDC
N,N-Dimethylformamide DMF
Electron spray ionisation Positive mode ESI+ or ESI
Electron spray ionisation Negative mode ESI–
Tetrahydrofuran THF
N,N,N',N'-Tetramethylethylendiamine TMEDA
Retention time Rt The following examples are part of and intended to illustrate but not limit the present invention.

EXAMPLE 1

2-Methyl-2-[(1-phenethyloxy-5,6,7,8-tetrahydro-naphthalene-2-carbonyl)-amino]-propionic acid

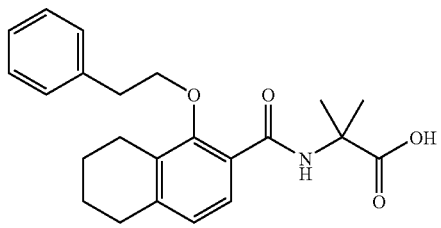 [SMILES: CC(C)(NC(=O)c1ccc2c(c1OCCc1ccccc1)CCCC2)C(=O)O]

a) 2-Methyl-2-[(1-phenethyloxy-5,6,7,8-tetrahydro-naphthalene-2-carbonyl)-amino]-propionic acid methyl ester 80 mg 2-[(1-hydroxy-5,6,7,8-tetrahydro-naphthalene-2-carbonyl)-amino]-2-methyl-pro-pionic acid methyl ester, 224 mg cesium carbonate, 61 mg of (2-bromoethyl)-benzene and 4 mg sodium iodide were dissolved in 5 ml of N,N-dimethylformamide and stirred at 80° C. for 6 h. 10 ml of diethyl ether and 10 ml of water were added to the reaction. The organic layer was separated and washed again with 10 ml of water. It was then dried over magnesium sulphate, filtered and concentrated in vacuo. Purification by flash chromatography (silica, heptanes/ethyl acetate) afforded 69 mg of 2-methyl-2-[(1-phenethyloxy-5,6,7,8-tetrahydro-naphthalene-2-carbonyl)-amino]-propionic acid methyl ester.

$C_{24}H_{29}NO_4$ (395.50), LCMS (ESI): 396.1 (MH$^+$).

b) 2-Methyl-2-[(1-phenethyloxy-5,6,7,8-tetrahydro-naphthalene-2-carbonyl)-amino]-propionic acid 65 mg 2-methyl-2-[(1-phenethyloxy-5,6,7,8-tetrahydro-naphthalene-2-carbonyl)-amino]-propionic acid methyl ester was dissolved in 2.5 ml of tetrahydrofuran and 0.25 ml of methanol. To this was added 0.25 ml of 2 M NaOH (aq), and the reaction was stirred overnight at room temperature. The reaction mixture was concentrated in vacuo, diluted with 5 ml of ethyl acetate and 5 ml of water and acidified to pH 3 with 1 N HCl (aq). The organic layer was separated, dried over magnesium sulphate and concentrated in vacuo. After purification by flash chromatography (silica, heptanes/ethyl acetate) 45 mg of 2-methyl-2-[(1-phenethyloxy-5,6,7,8-tetrahydro-naphthalene-2-carbonyl)-amino]-propionic acid were obtained.

$C_{23}H_{27}NO_4$ (381.48), LCMS (ESI): 382.1 (MH$^+$).

The following examples were prepared in analogy to example 1 via a sequence of an alkylation reaction to attach a suitably substituted alkylating agent to the aromatic hydroxy group of 2-[(1-hydroxy-5,6,7,8-tetrahydro-naphthalene-2-carbonyl)-amino]-2-methyl-propionic acid methyl ester or 2-[(7-Hydroxy-benzo[b]thiophene-6-carbonyl)-amino]-2-methyl-propionic acid methyl ester and a basic hydrolysis of the amino acid ester to the free amino acid:

| Example No. | Structure | Chemical Name | ESI+ or ESI– |
|---|---|---|---|
| 2 | 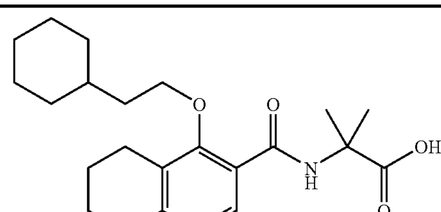 | 2-{[1-(2-Cyclohexyl-ethoxy)-5,6,7,8-tetrahydro-naphthalene-2-carbonyl]-amino}-2-methyl-propionic acid | 388.1 |
| 3 | 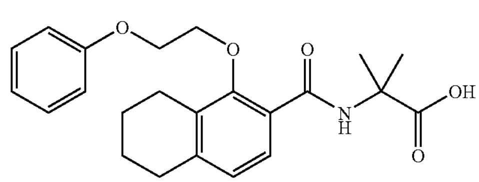 [SMILES: CC(C)(NC(=O)c1ccc2c(c1OCCOc1ccccc1)CCCC2)C(=O)O] | 2-Methyl-2-{[1-(2-phenoxy-ethoxy)-5,6,7,8-tetrahydro-naphthalene-2-carbonyl]-amino}-propionic acid | 398.1 |

-continued

| Example No. | Structure | Chemical Name | ESI+ or ESI− |
|---|---|---|---|
| 4 | 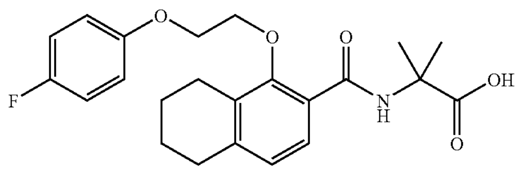 [SMILES: CC(C)(NC(=O)c1ccc2c(c1OCCOc1ccc(F)cc1)CCCC2)C(=O)O] | 2-({1-[2-(4-Fluoro-phenoxy)-ethoxy]-5,6,7,8-tetrahydro-naphthalene-2-carbonyl}-amino)-2-methyl-propionic acid | 416.0 |
| 5 | 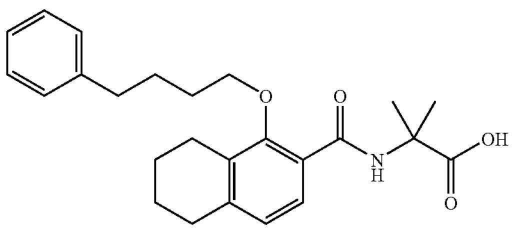 [SMILES: CC(C)(NC(=O)c1ccc2c(c1OCCCCc1ccccc1)CCCC2)C(=O)O] | 2-Methyl-2-{[1-(4-phenyl-butoxy)-5,6,7,8-tetrahydro-naphthalene-2-carbonyl]-amino}-propionic acid | 410.1 |
| 6 | 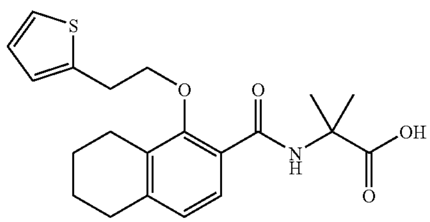 [SMILES: CC(C)(NC(=O)c1ccc2c(c1OCCc1cccs1)CCCC2)C(=O)O] | 2-Methyl-2-{[1-(2-thiophen-2-yl-ethoxy)-5,6,7,8-tetrahydro-naphthalene-2-carbonyl]-amino}-propionic acid | 388.05 |
| 7 | 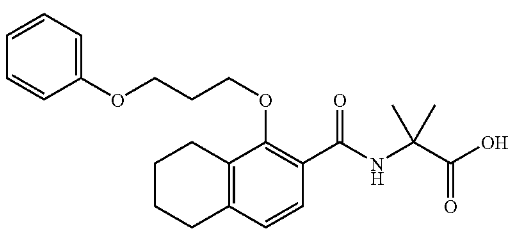 | 2-Methyl-2-{[1-(3-phenoxy-propoxy)-5,6,7,8-tetrahydro-naphthalene-2-carbonyl]-amino}-propionic acid | 412.15 |
| 8 | 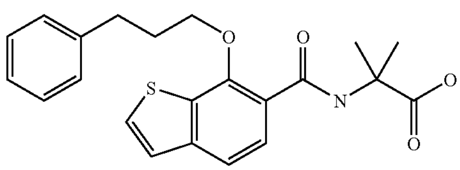 [SMILES: CC(C)(NC(=O)c1ccc2ccsc2c1OCCCc1ccccc1)C(=O)O] | 2-Methyl-2-{[7-(3-phenyl-propoxy)-benzo[b]thio-phene-6-carbonyl]-amino}-propionic acid | 398.25 |
| 9 | 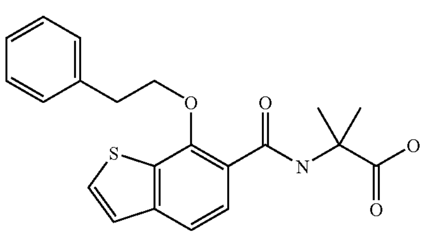 [SMILES: CC(C)(NC(=O)c1ccc2ccsc2c1OCCc1ccccc1)C(=O)O] | 2-Methyl-2-[(7-phenethyl-oxy-benzo[b]thiophene-6-carbonyl)-amino]-propionic acid | 384.27 |
| 10 | 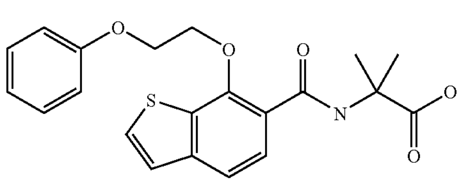 [SMILES: CC(C)(NC(=O)c1ccc2ccsc2c1OCCOc1ccccc1)C(=O)O] | 2-Methyl-2-{[7-(2-phenoxy-ethoxy)-benzo[b]thio-phene-6-carbonyl]-amino}-propionic acid | 400.21 |

| Example No. | Structure | Chemical Name | ESI+ or ESI− |
|---|---|---|---|
| 11 | 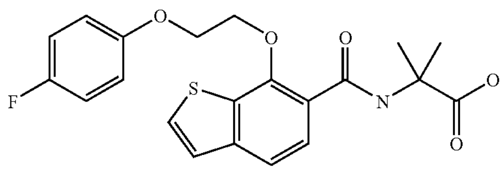 [SMILES: CC(C)(NC(=O)c1ccc2ccsc2c1OCCOc1ccc(F)cc1)C(=O)O] | 2-({7-[2-(4-Fluoro-phenoxy)-ethoxy]-benzo[b]thiophene-6-carbonyl}-amino)-2-methyl-propionic acid | 418.22 |

EXAMPLE 12

2-Methyl-2-{[4-(2-phenoxy-ethoxy)-benzo[b]thiophene-5-carbonyl]-amino}-propionic acid

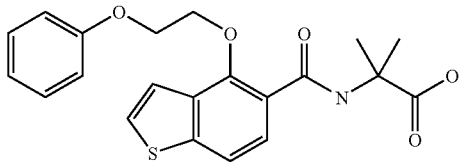 [SMILES: CC(C)(NC(=O)c1ccc2sccc2c1OCCOc1ccccc1)C(=O)O]

a) 2-[(4-Hydroxy-benzo[b]thiophene-5-carbonyl)-amino]-2-methyl-propionic acid tert-butyl ester To a solution of 300 mg 4-Hydroxy-benzo[b]thiophene-5-carboxylic acid in 5 ml N,N-dimethylformamide were added 42 mg 1-hydroxy-benzotriaziole and 285 mg 2-amino-2-methyl-propionic acid tert-butyl ester hydrochloride. At 0° C. 0.77 ml (600 mg) ethyl-diisopropyl-amine and 444 mg (3-dimethylamino-propyl)-ethyl-carbodiimide hydrochloride were added. After 16 h at room temperature 0.51 ml (400 mg) ethyl-diisopropyl-amine and 444 mg (3-dimethylamino-propyl)-ethyl-carbodiimide hydrochloride were added, and after additional 16 h the reaction was diluted with ethyl acetate and washed with brine. The organic layer was dried over magnesium sulphate and concentrated. The resulting residue was purified by flash chromatography (silica, heptane/ethyl acetate) to afford 315 mg 2-[(4-hydroxy-benzo[b]thiophene-5-carbonyl)-amino]-2-methyl-propionic acid tert-butyl ester.

$C_{17}H_{21}NO_4S$ (335.43), LCMS (ESI): 336.20 (MH+), 280.11 (MH+−tBu).

b) 2-Methyl-2-{[4-(2-phenoxy-ethoxy)-benzo[b]thiophene-5-carbonyl]-amino}-propionic acid tert-butyl ester 60 mg 2-[(4-Hydroxy-benzo[b]thiophene-5-carbonyl)-amino]-2-methyl-propionic acid tert-butyl ester, 70 mg cesium carbonate, 36 mg of (2-bromo-ethoxy)-benzene and 6 mg potassium iodide were dissolved in 1 ml of N,N-dimethylformamide and stirred for 2 h at 60° C. 10 ml of ethyl acetate and 10 ml of brine were added to the reaction. The organic layer was separated and washed again with 10 ml of brine. It was then dried over magnesium sulphate, filtered and concentrated in vacuo. The resulting residue was purified by reversed phase HPLC (acetonitrile/water) to afford 58 mg of 2-methyl-2-{[4-(2-phenoxy-ethoxy)-benzo[b]thiophene-5-carbonyl]-amino}-propionic acid tert-butyl ester.

$C_{25}H_{29}NO_5S$ (455.58), LCMS (ESI): 456.15.30 (MH+).

c) 2-Methyl-2-{[4-(2-phenoxy-ethoxy)-benzo[b]thiophene-5-carbonyl]-amino}-propionic acid 113 mg of 2-Methyl-2-{[4-(2-phenoxy-ethoxy)-benzo[b]thiophene-5-carbonyl]-amino}-propionic acid tert-butyl ester were dissolved in 2 ml dichloromethane and treated with 1 ml trifluoroacetic acid. After 6h at room temperature the volatiles were evaporated. The residue was treated with ethanol and 2 M HCl and evaporated three times. The resulting residue was crystallized from diethylether/heptane to afford 50 mg of 2-Methyl-2-{[4-(4-trifluoromethyl-benzyloxy)-benzo[b]thiophene-5-carbonyl]-amino}-propionic acid.

$C_{21}H_{21}NO_5S$ (399.47), LCMS (ESI): 400.23 (MH+).

Preparation of Intermediates:

2-[(1-Hydroxy-5,6,7,8-tetrahydro-naphthalene-2-carbonyl)-amino]-2-methyl-propionic acid methyl ester

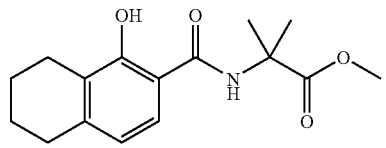 [SMILES: COC(=O)C(C)(C)NC(=O)c1ccc2c(c1O)CCCC2]

a) 5-Methoxymethoxy-1,2,3,4-tetrahydro-naphthalene 1.0 g 5,6,7,8-tetrahydro-naphthalen-1-ol was dissolved in 20 ml of N,N-dimethylform-amide. To this solution was added slowly 0.256 g of 95% NaH, followed by addition of 0.768 ml of chloromethoxymethane. The reaction was flushed with nitrogen and left stirring overnight at room temperature. The reaction mixture was then diluted with 50 ml of water and extracted with 50 ml of diethyl ether. The organic layer was washed with 50 ml of water, dried over magnesium sulphate and concentrated in vacuo to afford a crude oil. This was purified by flash chromatography (silica, heptanes/dichloro-methane) to afford 1.0 g of 5-methoxymethoxy-1,2,3,4-tetrahydro-naphthalene.

$C_{12}H_{16}O_2$ (192.11), LCMS (ESI): 161.1 (M+-OMe).

b) 1-Methoxymethoxy-5,6,7,8-tetrahydro-naphthalene-2-carboxylic acid

In a small round bottom flask was placed 0.2 g 5-methoxymethoxy-1,2,3,4-tetrahydro-naphthalene in 3 ml of anhydrous diethyl ether. This was cooled to 0° C. and flushed with nitrogen. Next, 0.98 ml of 1.6 M nbutyl-lithium was added by syringe followed by 0.156 ml of N,N,N',N'-tetramethylethylenediamine. The reaction was left stirring at 0° C. for 1 h, after which it was cooled to −78° C. and gaseous carbon dioxide was bubbled through for 15 min. The white suspension formed was warmed up to room temperature slowly and to it was added 10 ml of diethyl ether. The product was extracted with 20 ml of 1 M NaOH (aq.) and the aqueous layer was then acidified with NaHSO$_3$ to pH 2 and extracted twice with 20 ml of diethyl ether. The combined organic layers were dried over magnesium sulphate, filtered and concentrated in vacuo to give 0.21 g of 1-methoxymethoxy-5,6,7,8-tetrahydro-naphthalene-2-carboxylic acid.

$C_{13}H_{16}O_4$ (236.27) LC/MS (ESI) observed 259.0 (M+Na$^+$).

c) 2-[(1-Methoxymethoxy-5,6,7,8-tetrahydro-naphthalene-2-carbonyl)-amino]-2-methyl-propionic acid methyl ester In a round bottom flask was placed 0.96 g 1-methoxymethoxy-5,6,7,8-tetrahydro-naphthalene-2-carboxylic acid, 1.25 g 2-amino-2-methyl-propionic acid methyl ester hydrochloride, 3.09 g of O-(7-azabenzotriazole-1-yl)-N,N,N,N-tetramethyluronium hexafluoro phosphate and 2.83 ml of N,N-diisopropylethylamine in 60 ml of N,N-di-methylformamide. It was left stirring at room temperature overnight. 60 ml of diethylether and 60 ml of water were added to the reaction. The organic layer was separated and washed again with 50 ml of water. It was dried over magnesium sulphate, filtered and concentrated in vacuo to afford a crude yellow oil. Purification was performed by flash chromatography (silica, heptanes/ethyl acetate) to give 1.04 g 2-[(1-methoxymethoxy-5,6,7,8-tetrahydro-naphthalene-2-carbonyl)-amino]-2-methyl-propionic acid methyl ester.

$C_{18}H_{25}NO_5$ (335.17) LC/MS (ESI) observed 336.19 (M+H).

d) 2-[(1-Hydroxy-5,6,7,8-tetrahydro-naphthalene-2-carbonyl)-amino]-2-methyl-propionic acid methyl ester 1.023 g 2-[(1-methoxymethoxy-5,6,7,8-tetrahydro-naphthalene-2-carbonyl)-amino]-2-methyl-propionic acid methyl ester was dissolved in a mixture of isopropanol (8 ml), tetrahydrofurane (8 ml) and HCl conc. (4 ml). It was stirred at room temperature for one hour. The mixture was concentrated in vacuo, then 20 ml of ethyl acetate and 30 ml of water were added to the residue. The organic layer was separated, dried over magnesium sulphate and concentrated in vacuo to afford 0.857 g of 2-[(1-hydroxy-5,6,7,8-tetrahydro-naphthalene-2-carbonyl)-amino]-2-methyl-propionic acid methyl ester.

$C_{16}H_{21}NO_4$ (291.15), LC/MS (ESI) 292.15 (M+H).

2-[(7-Hydroxy-benzo[b]thiophene-6-carbonyl)-amino]-2-methyl-propionic acid methyl ester

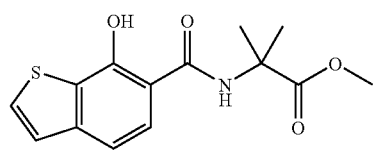 [SMILES: COC(=O)C(C)(C)NC(=O)c1ccc2ccsc2c1O]

To a solution of 1.40 g 7-hydroxy-benzo[b]thiophene-6-carboxylic acid in 20 ml N,N-dimethylformamide were added 0.21 g 1-hydroxy-benzotriazole and 1.42 g 2-amino-2-methyl-propionic acid methyl ester hydrochloride. At 0° C. 6.4 ml (4.99 g) ethyl-diiso-propyl-amine and 2.22 g (3-dimethylamino-propyl)-ethyl-carbodiimide hydrochloride were added. After 2 days at room temperature the reaction mixture was concentrated in vacuo, and the resulting residue was diluted with ethyl acetate and washed with brine. The organic layer was dried over magnesium sulphate and concentrated. The resulting residue was purified by flash chromatography (silica, heptane/ethyl acetate) to afford 0.84 g 2-[(7-hydroxy-benzo[b]thiophene-6-carbonyl)-amino]-2-methyl-propionic acid methyl ester.

$C_{14}H_{15}NO_4S$ (293.35), LC/MS (ESI) 294.13 (M+H).

The activity of the compounds of the present invention can be determined in the following manner.

Determination of CXCR2 Inhibition: Calcium Fluorescence Assay (FLIPR)

The assay is based on the detection of intracellular calcium changes detected by the selective, calcium-chelating dye, Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. Hence, influx of calcium to this cytoplasmic pocket, via release from intracellular pools and the phospholipase C cascade can be detected. By co-expressing the CXCR2 receptor and the promiscuous $G_{\alpha16}$ protein, activation of this chemokine receptor is directed into this phospholipase C cascade resulting in intracellular calcium mobilization.

The CHO-K1 cells stably transfected with human CXCR2 and the promiscuous $G_{\alpha16}$ protein are maintained in a log phase of growth at 37° C. and 5% CO$_2$ in the following media: Iscove's, 10% FBS, 1X Penicillin-Streptomycin, 400 µg/ml G418 and 350 µg/ml Zeocin. Approximately 24-48 hours prior to the assay, 20,000-30,000 cells/well are plated onto a 96-well black/clear bottomed assay plate (Becton Dickinson) with a well volume of 180 µl. For dye loading the culture medium is carefully removed and replaced by 100 µl/well dye solution (4 µM Fluo-4 in 135 mM NaCl, 5 mM KCl, 1 mM magnesium sulphate, 5 mM glucose, 20 mM hepes, 2.5 mM probenecid; pH 7.4). Cells are incubated for 1 h at 37° C., and then washed 3× with buffer. After washing 90 µl buffer/well are left. Increasing concentrations of compound is added in 45 µl buffer (4× concentrated) followed by 10 min incubation at 37° C. Then the chemokine (10-100 nM) is applied in 45 µl buffer (4× concentrated) and the measurement is performed for 2 min. The IC50 value of a compound can be determined by calculation of % inhibition of total calcium response to the chemokine.

CXCR2 Inhibition with Chemokine IL-8 for Selected Example Compounds:

| Example No. | IC50 [µM] |
| --- | --- |
| 2 | 1.4 |
| 3 | 1.0 |
| 5 | 2.0 |
| 7 | 2.1 |
| 8 | 0.6 |
| 11 | 0.8 |
| 12 | 1.7 |

The invention claimed is:
1. A compound of formula I:

I wherein:
X is —CR3=CR4-, —NR7-, or —S—;
wherein R3 and R4 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_OR32$, $S(O)_pNR33R34$, aryl, heteroaryl, arylalkyl with alkyl having 1, 2, 3 or 4 carbon atoms or heteroarylalkyl with alkyl having 1, 2, 3 or 4 carbon atoms;
wherein R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34 are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl; and
o and p are, independently of one another, 1 or 2;
R7 is hydrogen, alkyl having 1, 2, 3 or 4 carbon atoms or C(O)R35;
wherein R35 is hydrogen, alkyl with 1, 2, 3 or 4 carbon atoms or aryl;
Y is —C(R61R62)-C(R61R62)-C(R61R62)-, —S(O)$_u$—C(R63R64)-C(R61R62)-, —C(R63R64)-S(O)$_u$—C(R63R64)-, —C(R61R62)-C(R63R64)-S(O)$_u$—C(R61R62)-C(R61R62)-C(R61R62)-C(R61R62)-, —S(O)$_u$—C(R63R64)-C(R61R62)-C(R61R62)-, —C(R63R64)-S(O)$_u$—C(R63R64)-C(R61R62)-, —C(R61R62)-C(R63R64)-S(O)$_u$—C(R63R64)-, —C(R61R62)-C(R61R62)-C(R63R64)-S(O)$_u$—, —S(O)$_u$—C(R63R64)-C(R63R64)-S(O)$_u$—, —S(O)$_v$—CR65=CR66- or —CR67=CR68-S(O)V—;
wherein R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;
R62, R63 and R64 are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen;
R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$;
u is 0, 1 or 2; and
v is 0, 1 or 2;
A is cycloalkyl having 3, 4, 5, 6, 7 or 8 carbon atoms, heterocyclyl having 5, 6, 7 or 8 atoms, phenyl or heteroaryl having 5 or 6 atoms;
in which the said cycloalkyl, heterocyclyl, phenyl or heteroaryl can be condensed to a cycloalkyl radical having 3, 4, 5, 6, 7 or 8 atoms, a heterocyclyl radical having 5, 6, 7 or 8 atoms, or a phenyl radical or a heteroaryl radical having 5 or 6 atoms,
and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is a linear linker consisting of 3, 4 or 5 carbon atoms, in which 1 or 2 carbon atoms can be replaced by a member of a heteroatom containing group consisting of O, NR19 or $S(O)_y$, and which linker may contain 0, 1 or 2 double or triple bonds between carbon atoms within the linker, with the provisos, that 2 of said heteroatom containing groups are separated by at least 2 carbon atoms, that heteroatom containing groups are not adjacent to a double or triple bond within the linker or to a non-aromatic double bond, which might be part of A, that double or triple bonds are not cumulated, and that, if A is connected to the linker via a nitrogen atom being part of A, the atom of the linker which is connected to A is a carbon atom;

and in which linker saturated carbon atoms, which are not adjacent to heteroatom containing groups, which are not adjacent to double or triple bonds within the linker or which are not adjacent to a heteroatom, which might be part of A, can, independently of one another, be substituted by hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms; cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

and in which linker saturated carbon atoms, which are adjacent to heteroatom containing groups, which are adjacent to double or triple bonds in the linker, or which are adjacent to a heteroatom, which might be part of A, or carbon atoms being part of a double bond, can, independently of one another, be substituted by hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

wherein R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms; and y is 0, 1 or 2;

R1 is hydrogen or alkyl having 1, 2, 3, 4, 5 or 6 carbon atoms;

which can be unsubstituted or substituted by 1, 2, 3, 4 or 5 radicals selected from the group consisting of F, Cl, Br, I, and $—O_i—(CH_2)_j—R25$;

wherein i is 0 or 1;

j is 0, 1, 2 or 3; and

R25 is hydrogen, phenyl, heteroaryl having 5 or 6 atoms, cycloalkyl having 3, 4, 5 or 6 carbon atoms or heterocyclyl having 3, 4, 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I;

R2 is alkyl having 1, 2, 3, 4, 5 or 6 carbon atoms, phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein alkyl is unsubstituted or substituted by 1, 2, 3, 4 or 5 radicals selected from the group consisting of F, Cl, Br, I, and $—O_m—(CH_2)_n—R26$;

wherein m is 0, or 1;

n is 0, 1, 2 or 3; and

R26 is hydrogen, phenyl, heteroaryl having 5 or 6 atoms, cycloalkyl having 3, 4, 5 or 6 carbon atoms or heterocyclyl having 3, 4, 5, 6, 7 or 8 atoms, in which the phenyl, heteroaryl, cycloalkyl or heterocyclyl are unsubstituted or substituted by 1, 2, or 3 radicals selected from the group consisting of F, Cl, Br and I;

and wherein said phenyl, heteroaryl having 5 or 6 atoms, cycloalkyl having 3, 4, 5, 6, 7 or 8 carbon atoms or heterocyclyl having 3, 4, 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; or R1 and R2 form, together with the carbon atom to which they are attached, a 3-, 4-, 5- or 6-membered carbon ring, wherein one carbon atom, which is not adjacent to the carbon atom, to which R1 and R2 are attached, can be replaced by —O—, —NR58- or $—S(O)_w—$, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;
wherein the formed ring and the condensed phenyl, heteroaryl, cycloalkyl or heterocyclyl radical can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;
R58 is hydrogen, alkyl having 1, 2, 3 or 4 carbon atoms or C(O)R59;
wherein R59 is hydrogen, alkyl with 1, 2, 3 or 4 carbon atoms or phenyl; and
w is 0, 1 or 2;
or a pharmaceutically acceptable salt thereof.

2. A compound of formula I as claimed in claim 1, wherein:
X is —CR3=CR4-, —NR7- or —S—;
wherein R3 and R4 are, independently of one another, hydrogen, F, Cl, Br, I, alkyl having 1, 2, 3 or 4 carbon atoms or alkoxy having 1, 2, 3 or 4 carbon atoms; and
R7 is hydrogen or alkyl having 1, 2, 3 or 4 carbon atoms;
Y is —C(R61R62)-C(R61R62)-C(R61R62)-, —S—C(R63R64)-C(R61R62)-, —C(R63R64)-S—C(R63R64)-, —C(R61R62)-C(R63R64)-S—, —C(R61R62)-C(R61R62)-C(R61R62)-C(R61R62)-, —S—C(R63R64)-C(R61R62)-C(R61R62)-, —C(R63R64)-S—C(R63R64)-C(R61R62)-, —C(R61R62)-C(R63R64)-S—C(R63R64)-, —C(R61R62)-C(R61R62)-C(R63R64)-S—, —S—C(R63R64)-C(R63R64)-S—, —S—CR65=CR66- or —CR67=CR68-S—;
wherein R61 is hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, CN or $SCF_3$;
R62, R63 and R64 are, independently of one another hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
with the proviso, that in any embodiment of Y a maximum of 4 of the substituents R61 to R64 are not hydrogen; and
R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms; OH, $NO_2$, CN or $SCF_3$;
A is cycloalkyl having 3, 4, 5, 6, 7 or 8 carbon atoms, heterocyclyl having 5, 6, 7 or 8 atoms, phenyl or heteroaryl having 5 or 6 atoms;
in which the said phenyl can be condensed to a cycloalkyl radical having 3, 4, 5, 6, 7 or 8 atoms, a heterocyclyl radical having 5, 6, 7 or 8 atoms, a phenyl radical or a heteroaryl radical having 5 or 6 atoms,
and in which said cycloalkyl, heterocyclyl, phenyl or heteroaryl and the optionally condensed cycloalkyl radical, heterocyclyl radical, phenyl radical or heteroaryl radical are unsubstituted or substituted by 1, 2, 3, 4 or 5 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, and —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
B is —C(R11R12)-C(R13R14)-O—, —C(R11R12)-C(R15R16)-C(R15R16)-, —C(R13R14)-C≡C—, —C(R13R14)-C(R17)=C(R18)-, —C(R11R12)-C(R13R14)-NR19-, —C(R11R12)-C(R13R14)-S(O)$_y$—, —O—C(R13R14)-C(R15R16), —C≡C—C(R13R14)-, —C(R17)=C(R18)-C(R13R14)-, —C(R13R14)-O—C(R13R14)-, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R13R14)-O—C(R13R14)-C(R15R16)-, —C(R11R12)-C(R13R14)-O—C(R13R14)-, —C(R11R12)-C(R15R16)-C(R13R14)-S(O)$_y$—, —O—C(R13R14)-C(R13R14)-S(O)$_y$—, —O—C(R13R14)-C(R17)=C(R18)-, —C≡C—C(R13R14)—C(R15R16)-, —C(R17)=C(R18)-C(R13R14)-C(R15R16)-, —C(R13R14)-C≡C—C(R13R14)-, —C(R13R14)-C(R17)=C(R18)-C(R13R14)-, —C(R11R12)-C(R15R16)-C(R15R16)-C(R15R16)-C (R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C—, —C(R13R14)-O—C(R13R14)-C(R13R14)-O—, —C(R13R14)-O—C(R13R14)-C(R15R16)-C(R15R16)-, —C(R11R12)-C(R15R16)-C(R13R14)-C(R17)=C(R18)-, —C(R13R14)-C(R17)=C(R18)-C(R13R14)-O—, —C(R13R14)-C≡C—C(R13R14)-O—, —C(R17)=C(R18)-C(R13R14)-C(R13R14)-O—, —C≡C—C(R13R14)-C(R13R14)-O—; —C(R11R12)-C(R15R16)-C(R13R14)-O—C(R13R14)-, —C(R11R12)-C(R13R14)-O—C(R13R14)-C(R15R16)-, —O—C(R13R14)-C(R15R16)-C(R15R16)-C(R15R16)- or —O—C(R13R14)-C(R13R14)-O—C(R13R14)-;

with the proviso that, if A is connected to the linker B via a nitrogen atom being part of A, the atom of the linker which is connected to A is a carbon atom;

R11 and R12 are, independently of one another, hydrogen, F, OH, alkyl having 1, 2, 3, 4, 5 or 6 carbon atoms, in which 1, 2, 3, 4, 5,6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

with the proviso that, if B is attached to a nitrogen atom being part of A, R11 or R12 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R13, R14, R17 and R18 are, independently of one another, hydrogen, F, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms or cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R15 and R16 are, independently of one another, hydrogen, F, OH, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or cycloalkoxy having 3, 4, 5 or 6 carbon atoms, in which 1, 2, 3, 4, 5, 6, 7, 8, 9, 10 or 11 hydrogen atoms may be substituted by fluorine atoms, cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

R19 is hydrogen, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, C(O)R44 or C(O)NR45R46;

wherein R44, R45 and R46 are, independently of one another, hydrogen, alkyl having 1, 2, 3 or 4 carbon atoms, in which 1, 2, 3, 4, 5, 6 or 7 hydrogen atoms may be substituted by fluorine atoms or cycloalkyl having 3 or 4 carbon atoms, in which 1, 2, 3, 4, 5 or 6 hydrogen atoms may be substituted by fluorine atoms; and y is 0, 1 or 2;

R1 is hydrogen or alkyl having 1, 2, 3, 4, 5 or 6 carbon atoms; and

R2 is alkyl having 1, 2, 3, 4, 5 or 6 carbon atoms or phenyl, wherein said alkyl is unsubstituted or substituted by 1, 2, 3, 4 or 5 radicals selected from the group consisting of F, Cl, Br, I, and —$O_m$—$(CH_2)_n$—R26;

wherein m is 0, or 1;

n is 0, 1, 2 or 3; and

R26 is hydrogen, phenyl, heteroaryl having 5 or 6 atoms, cycloalkyl having 3, 4, 5 or 6 carbon atoms or heterocyclyl having 3, 4 5, 6, 7 or 8 atoms; in which the phenyl, heteroaryl, cycloalkyl or heterocyclyl are unsubstituted or substituted by 1, 2, or 3 radicals selected from the group consisting of F, Cl, Br and I; or R1 and R2 form, together with the carbon atom to which they are attached, a 3-, 4-, 5- or 6membered saturated or partly saturated carbon ring, which can be condensed to phenyl; or R1 and R2 form, together with the carbon atom to which they are attached, a 4-, 5- or 6-membered saturated or partly saturated carbon ring, wherein one carbon atom, which is not adjacent to the carbon atom, to which R1 and R2 are attached, is replaced by —O—, —NH— or —S—;

or a pharmaceutically acceptable salt thereof.

3. A Compound of the formula I as claimed in claim 1, wherein:

X is —CR3=CR4-, —NH— or —S—;

wherein R3 and R4 are, independently of one another, hydrogen, F, Cl or Br;

Y is —C(R61R62)-C(R61R62)-C(R61R62)-,
—S—C(R63R64)-C(R61R62)-,
—C(R63R64)-S—C(R63R64)-,
—C(R61R62)-C(R63R64)-S—,
—C(R61R62)-C(R61R62)-C(R61R62)-C(R61R62)-,
—S—C(R63R64)-C(R61R62)-C(R61R62)-,
—C(R63R64)-S—C(R63R64)-C(R61R62)-,
—C(R61R62)-C(R63R64)-S—C(R63R64)-,
—C(R61R62)-C(R61R62)-C(R63R64)-S—,
—S—C(R63R64)-C(R63R64)-S—,
—S—CR65=CR66- or
—CR67=CR68-S—;

wherein R61, R62, R63 and R64 are, independently of one another hydrogen, F or alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

with the proviso, that in any embodiment of Y a maximum of 4 of the substituents R61 to R64 are not hydrogen;

R65, R66, R67 and R68 are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms or alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

A is cycloalkyl having 3, 4, 5, 6, 7 or 8 carbon atoms, heterocyclyl having 5, 6, 7 or 8 atoms, phenyl or heteroaryl having 5 or 6 atoms;

in which the said phenyl can be condensed to form a naphthyl or an indanyl;

in which said cycloalkyl, heterocyclyl, phenyl, heteroaryl or the optionally formed naphthyl or indanyl are unsubstituted or substituted by 1, 2, 3, 4 or 5 radicals selected from the group consisting of F, Cl, Br, I, OH, CN, $NO_2$, $SF_5$, $SCF_3$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms and alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

B is —C(R11R12)-C(R13R14)-O—, —C(R11R12)-C(R15R16)-C(R13R14)-O—, —C(R11R12)-C(R15R16)-C(R13R14)-NR19-, —C(R11R12)-C(R15R16)-C(R15R16)-C(R15R16)-, —O—C(R13R14)-C(R13R14)-O—, —O—C(R13R14)-C(R13R14)-NR19-, —O—C(R13R14)-C(R15R16)-C(R15R16)-, —C(R17)=C(R18)-C(R13R14)-O—, —C≡C—C(R13R14)-O—, —C(R11R12)-C(R13R14)-C(R17)=C(R18)-, —C(R11R12)-C(R13R14)-C≡C—, —O—C(R13R14)-C≡C—, —C(R11R12)-C(R15R16)-C(R15R16)-C(R15R16)-C(R15R16)-, —C(R11R12)-C(R15R16)-C(R15R16)-C(R13R14)-O—, —O—C(R13R14)-C(R15R16)-C(R13R14)-O—, —C(R11R12)-C(R15R16)-C(R13R14)-C≡C— or —C(R13R14)-O—C(R13R14)-C(R13R14)-O—, with the proviso that, if A is connected to the linker B via a nitrogen atom being part of A, the atom of the linker which is connected to A is a carbon atom;

R11-R18 are, independently of one another, hydrogen, F or alkyl having 1, 2, 3, 4 carbon atoms; and R19 is H or alkyl having 1, 2, 3, 4, 5 or 6 carbon atoms;

R1 is alkyl having 1, 2, 3 or 4 carbon atoms; and

R2 is alkyl having 1, 2, 3 or 4 carbon atoms, phenyl or benzyl; or

R1 and R2 form, together with the carbon atom to which they are attached, a cyclopropane, cyclobutane, cyclopentane, cyclohexane, cyclopentene ring or indene; or R1 and R2 form, together with the carbon atom to which they are attached, a tetrahydro thiophene or tetrahydrothiopyrane ring;

or a pharmaceutically acceptable salt thereof.

4. A Compound of the formula I as claimed in claim 1, wherein

X is —CR3=CR4- or —S—;

wherein R3 and R4 are, independently of one another, hydrogen, F, Cl or Br;

Y is —C(R61R62)-C(R61R62)-C(R61R62)-, —C(R61R62)-C(R61R62)-C(R61R62)-C(R61R62)-, —S—CR65=CR66- or —CR67=CR68-S—;

wherein R61 and R62 are, independently of one another, hydrogen, F or alkyl having 1, 2, 3 or 4 carbon atoms;

with the proviso, that in any embodiment of Y a maximum of 4 of the substituents R61 to R62 are not hydrogen; and R65, R66, R67 and R68 are, independently of one another, hydrogen, F, Cl, Br, I, alkyl having 1, 2, 3 or 4 carbon atoms;

A is cyclohexyl, phenyl, naphthyl, indanyl or thienyl;

in which the phenyl radical is unsubstituted or substituted by 1, 2 or 3 radicals selected from the group consisting of F, Cl, Br, methoxy, methyl, ethyl, propyl, iso-propyl and trifluoromethyl;

B is —C(R11R12)-C(R13R14)-O—, —C(R11R12)-C(R15R16)-C(R13R14)-O—, —O—C(R13R14)-C(R13R14)-O—, —C(R11R12)-C(R15R16)-C(R15R16)-C(R13R14)-O—, —O—C(R13R14)-C(R15R16)-C(R13R14)-O—, or —C(R13R14)-O—C(R13R14)-C(R13R14)-O—, wherein R11-R16 are, independently of each other, hydrogen or methyl;

R1 is methyl or ethyl; and

R2 is methyl or ethyl;

or R1 and R2 form, together with the carbon atom to which they are attached, a cyclobutane or cyclopentane ring;

or a pharmaceutically acceptable salt thereof.

5. A compound of the formula I as claimed in claim 1, wherein:

X is —CR3=CR4-;

wherein R3 and R4 are, independently of one another, hydrogen or F;

Y is —C(R61R62)-C(R61R62)-C(R61R62)-C(R61R62)-, —S—CR65=CR66- or

—CR67=CR68-S—;

wherein R61 and R62 are, independently of one another, hydrogen or F;

with the proviso, that in any embodiment of Y a maximum of 4 of the substituents R61 to R62 are not hydrogen; and R65, R66, R67 and R68 are, independently of one another, hydrogen, F, Cl, Br, I, alkyl having 1, 2, 3 or 4 carbon atoms;

A is cyclohexyl, phenyl or thienyl;

in which the phenyl radical is unsubstituted or substituted by 1, 2 or 3 radicals selected from the group consisting of F, Cl, Br, methoxy, methyl, ethyl, propyl, iso-propyl and trifluoromethyl;

B is —C(R11R12)-C(R13R14)-O—, —C(R11R12)-C(R15R16)-C(R13R14)-O—, —O—C(R13R14)-C(R13R14)-O—, —C(R11R12)-C(R15R16)-C(R15R16)-C(R13R14)-O or —O—C(R13R14)-C(R15R16)-C(R13R14)-O—;

wherein R11-R16 are, independently of each other, hydrogen or methyl;

R1 is methyl; and

R2 is methyl or ethyl;

or a pharmaceutically acceptable salt or a prodrug thereof.

6. A compound of formula I as claimed in claim 1 selected from the group consisting of:

2-Methyl-2-[(1-phenethyloxy-5,6,7,8-tetrahydro-naphthalene-2-carbonyl)-amino]-propionic acid, 2-{[1-(2-Cyclohexyl-ethoxy)-5,6,7,8-tetrahydro-naphthalene-2-carbonyl]-amino}-2-methyl-propionic acid, 2-Methyl-2-{[1-(2-phenoxy-ethoxy)-5,6,7,8-tetrahydro-naphthalene-2-carbonyl]-amino}-propionic acid, 2-({1-[2-(4-Fluoro-phenoxy)-ethoxy]-5,6,7,8-tetrahydro-naphthalene-2-carbonyl}-amino)-2-methyl-propionic acid,
2-Methyl-2-{[1-(4-phenyl-butoxy)-5,6,7,8-tetrahydro-naphthalene-2-carbonyl]-amino}-propionic acid,
2-Methyl-2-{[1-(2-thiophen-2-yl-ethoxy)-5,6,7,8-tetrahydro-naphthalene-2-carbonyl]-amino}-propionic acid,
2-Methyl-2-{[1-(3-phenoxy-propoxy)-5,6,7,8-tetrahydro-naphthalene-2-carbonyl]-amino}-propionic acid,
2-Methyl-2-{[7-(3-phenyl-propoxy)-benzo[b]thiophene-6-carbonyl]-amino}-propionic acid,
2-Methyl-2-[(7-phenethyloxy-benzo[b]thiophene-6-carbonyl)-amino]-propionic acid,
2-Methyl-2-{[7-(2-phenoxy-ethoxy)-benzo[b]thiophene-6-carbonyl]-amino}-propionic acid,
2-({7-[2-(4-Fluoro-phenoxy)-ethoxy]-benzo[b]thiophene-6-carbonyl}-amino)-2-methyl-propionic acid, and
2-Methyl-2-{[4-(2-phenoxy-ethoxy)-benzo[b]thiophene-5-carbonyl]-amino}-propionic acid,
or a pharmaceutically acceptable salt thereof.

7. A compound of the formula I or a pharmaceutically acceptable salt as claimed in claim 1 for use as medicament.

8. A method for treating a chemokine mediated disease, the method comprising administering to a patient in need thereof an effective amount of a compound of claim 1, wherein Y is selected from —C(R61R62)-C(R61R62)- C(R61R62)-C(R61R62)- , —S—CR65=CR66-, and —CR67=CR68-S—, and R61, R62, and R65-R68 are as defined in claim 1.

9. A method for treating acute and chronic inflammatory diseases, the method comprising administering to a patient in need thereof an effective amount of a compound of claim 1, wherein Y is selected from —C(R61R62)-C(R61R62)-C(R61R62)-C(R61R62)-, —S—CR65=CR66-, and —CR67=CR68-S—, and R61, R62, and R65-R68 are as defined in claim 1, wherein said acute and chronic inflammatory diseases are chemokine mediated diseases wherein the chemokine in said chemokine mediated disease binds to a CXCR2 receptor, and said compound of claim 1 is a CXCR2 receptor inhibitor.

10. The method of claim 8, wherein said chemokine mediated disease is selected from arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgerical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration, corneal neovasularization, tumor angiogenesis, cancer and metastasis.

11. The method of claim 8, wherein said chemokine mediated disease is selected from atherosclerosis, ischemia/reperfusion injuries, chronic obstructive pulmonary disease, asthma, and rheumatoid arthritis, adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis and cancer.

12. A pharmaceutical composition comprising an effective amount of a compound of claim 1 or a pharmaceutically acceptable salt thereof and a pharmaceutically acceptable carrier.

13. A pharmaceutical composition comprising an effective amount of a compound of claim 1 or a pharmaceutically acceptable salt thereof and a pharmaceutically acceptable carrier in combination with at least one other pharmacological active ingredient.

14. The method of claim 10, wherein said macular degeneration is wet type.

15. The method of claim 8, wherein the chemokine in said chemokine mediated disease binds to a CXCR2 receptor, and said compound of claim 1 is a CXCR2 receptor inhibitor.

* * * * *

UNITED STATES PATENT AND TRADEMARK OFFICE
CERTIFICATE OF CORRECTION

PATENT NO. : 8,980,938 B2
APPLICATION NO. : 12/337980
DATED : March 17, 2015
INVENTOR(S) : Stephanie Hachtel et al.

It is certified that error appears in the above-identified patent and that said Letters Patent is hereby corrected as shown below:

On the Title Page In Other Publications:

Page two, column 1, line 5, please replace "Ochratoxin a" with --Ochratoxin A--.

In the Claims:

At column 51, claim number 1, line number 5, please replace

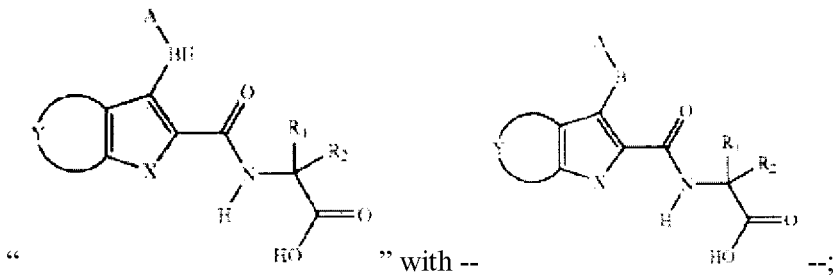

At column 51, claim number 1, line numbers 53-54, please replace "–C(R61R62)-C(R63R64)S(O)u—C(R61R62)-C(R61R62)-C(R61R62)-C(R61R62)-," with -- –C(R61R62)-C(R63R64)S(O)u-, -C(R61R62)-C(R61R62)-C(R61R62)-C(R61R62)-,--;

At column 51, claim number 1, line number 60, please replace "-CR67=CR68-S(O)V-;" with ---CR67=CR68-S(O)v-;--;

At column 52, claim number 1, line number 21, please replace "ofY" with --of Y--;

At column 55, claim number 2, line number 15, please replace "-NR7-" with --NR7- --;

At column 55, claim number 2, line number 57, please replace "ofY" with --of Y--;

Signed and Sealed this
Twenty-fifth Day of August, 2015

Michelle K. Lee
*Director of the United States Patent and Trademark Office*

CERTIFICATE OF CORRECTION (continued)
U.S. Pat. No. 8,980,938 B2

At column 58, claim number 2, line number 36, please replace "3, 4 5," with --3, 4, 5,--;

At column 58, claim number 2, line number 41, please replace "3-, 4, 5- or 6membered" with --3-, 4-, 5- or 6-membered--;

At column 58, claim number 3, line number 51, please replace "Compound" with --compound--;

At column 59, claim number 3, line number 57, please replace "ofY" with --of Y--;

At column 59, claim number 4, line number 63, please replace "Compound" with --compound--; and At column 60, claim number 4, line number 6, please replace "ofY" with --of Y--.